(12) United States Patent
Fehler et al.

(10) Patent No.: US 9,073,979 B2
(45) Date of Patent: Jul. 7, 2015

(54) VACCINATION AGAINST HOST CELL-ASSOCIATED HERPES VIRUSES

(75) Inventors: Frank Fehler, Cuxhaven (DE); Klaus Osterrieder, Insel Riems (DE)

(73) Assignee: Lohmann Animal Health GmbH, Indianapolis, IN (US)

( * ) Notice: Subject to any disclaimer, the term of this patent is extended or adjusted under 35 U.S.C. 154(b) by 1696 days.

(21) Appl. No.: 10/354,932

(22) Filed: Jan. 30, 2003

(65) Prior Publication Data

US 2003/0165537 A1    Sep. 4, 2003

Related U.S. Application Data

(63) Continuation of application No. PCT/EP01/08893, filed on Aug. 1, 2001.

(30) Foreign Application Priority Data

Aug. 3, 2000    (EP) ..................................... 00202757

(51) Int. Cl.

| | | |
|---|---|---|
| A61K 39/12 | (2006.01) | |
| A61K 39/245 | (2006.01) | |
| C12P 21/06 | (2006.01) | |
| C12N 15/00 | (2006.01) | |
| C12N 15/09 | (2006.01) | |
| C12N 15/63 | (2006.01) | |
| C12N 15/74 | (2006.01) | |
| C12N 15/70 | (2006.01) | |
| C07K 14/005 | (2006.01) | |
| A61K 39/00 | (2006.01) | |

(52) U.S. Cl.
CPC ......... *C07K 14/005* (2013.01); *A61K 2039/523* (2013.01); *A61K 2039/5256* (2013.01); *A61K 2039/53* (2013.01); *C07K 2319/00* (2013.01); *C12N 2710/16322* (2013.01)

(58) Field of Classification Search
None
See application file for complete search history.

(56) References Cited

U.S. PATENT DOCUMENTS

| | | | |
|---|---|---|---|
| 5,558,867 A | 9/1996 | Sakaguchi et al. | |
| 6,306,387 B1 | 10/2001 | Galan | |

FOREIGN PATENT DOCUMENTS

| | | |
|---|---|---|
| EP | 522 535 A1 | 7/1992 |
| JP | 5-292976 | 11/1993 |
| JP | 09-009978 | 1/1997 |
| JP | 11509099 T | 8/1999 |
| JP | 11-313690 | 11/1999 |
| JP | 2000-166582 | 6/2000 |
| JP | 2002541797 T | 12/2002 |
| WO | WO 98 53854 | 5/1998 |
| WO | WO 99/06582 | 7/1998 |
| WO | WO 00/35476 | 12/1999 |
| WO | WO 00/26396 | 5/2000 |
| WO | WO 02/012288 A2 | 2/2002 |

OTHER PUBLICATIONS

Greenspan et al. (Nature Biotechnology 7: 936-937, 1999).*
Bowie et al (Science, 1990, 257:1306-1310).*
Becker et al. (Acta Virologica, 1999, vol. 43 pp. 81-89.*
Anderson et al., The Glycoprotein D (US6) Homolog Is Not Essential for Oncogenicity or Horizontal Transmission of Marek's Disease Virus, Journal of Virology, Mar. 1998, pp. 2548-2553, vol. 72, No. 3.
Dolan et al., The Genome Sequence of Herpes Simplex Virus Type 2, Journal of Virology, Mar. 1998, pp. 2010-2021, vol. 72, No. 3.
Lee et al., The complete unique long sequence and the overall genomic organization of the GA strain of Marek's disease virus, PNAS, May 23, 2000, pp. 6091-6096, vol. 97, No. 11.
Mao et al., Quantitative evaluation of viral fitness due to a single nucleotide polymorphism in the Marek's disease virus UL41 gene via an in vitro competition assay, Journal of Virological Methods, 2008, pp. 125-131, vol. 148.
Osterrieder et al., The genome content of Marek's disease-like viruses, Elsevier Ltd, 2004.
Reddy et al., Rescue of a pathogenic Marek's disease virus with overlapping cosmid DNAs: Use of a pp38 mutant to validate the technology for the study of gene function, PNAS, May 14, 2002, pp. 7054-59, vol. 99, No. 10.
Thale et al., Identification of the Mouse Cytomegalovirus Genomic Region Affecting Major Histocompatibility Complex Class I Molecule Transport, Journal of Virology, Oct. 1995, pp. 6098-6105, vol. 69, No. 10.
Saeki et al., Herpes Simplex Virus Type 1 DNA Amplified as Bacterial Artificial Chromosome in *Escherichia coli*: Rescue of Replication-competent Virus Progeny and Packaging of Amplicon Vectors, Human Gene Therapy, Dec. 10, 1998, pp. 2787-2794, vol. 9.
Tischer et al., "A DNA vaccine containing an infectious Marek's disease virus genome can confer protection against tumorigenic Marek's disease in chickens," Journal of General Virology, 2002, pp. 2367-2376, vol. 83.
Biggs, PM., "The history and biology of Marek's disease virus," paragraph 2.3 on pp. 6-7. Published in "Marek's disease," Ed Hirai, K; Springer Verlag. 2001.
Roizman, B., "Herpesviridae," published as Chapter 71 in "Virology," Eds Fields BM, Knipe DM, and Howley PM, Lippincott-Raven publishers, Philadelphia, Aug. 2001.
International Search Report. International Publication No. PCT EPO1 08893 dated Feb. 12, 2002 (3 pages).
Tsukamoto et al, Protection of Chickens against Very Virulent Infectious Dorsal Disease Virus (IBDV) and Marek's Disease Virus (MDV) with a Recombinant MDV Expressing IBDV VP2, Virology, 1999, pp. 352-62, vol. 257.

(Continued)

*Primary Examiner* — Robert A Zeman
(74) *Attorney, Agent, or Firm* — David L. Pflugh

(57) ABSTRACT

The invention relates to the field of so-called "host cell-associated herpes viruses," such as Marek's disease-like virus (MDV) of poultry and Varicella Zoster virus (VZV) of man, and to vaccination against disease caused by these viruses. The invention provides a vaccine directed against an infection caused by a herpes virus that is essentially host cell-associated comprising a recombinant viral genome derived from the herpes virus, the genome allowing recombination essentially free of the host cell.

7 Claims, 10 Drawing Sheets

(56) References Cited

OTHER PUBLICATIONS

Figure 1:
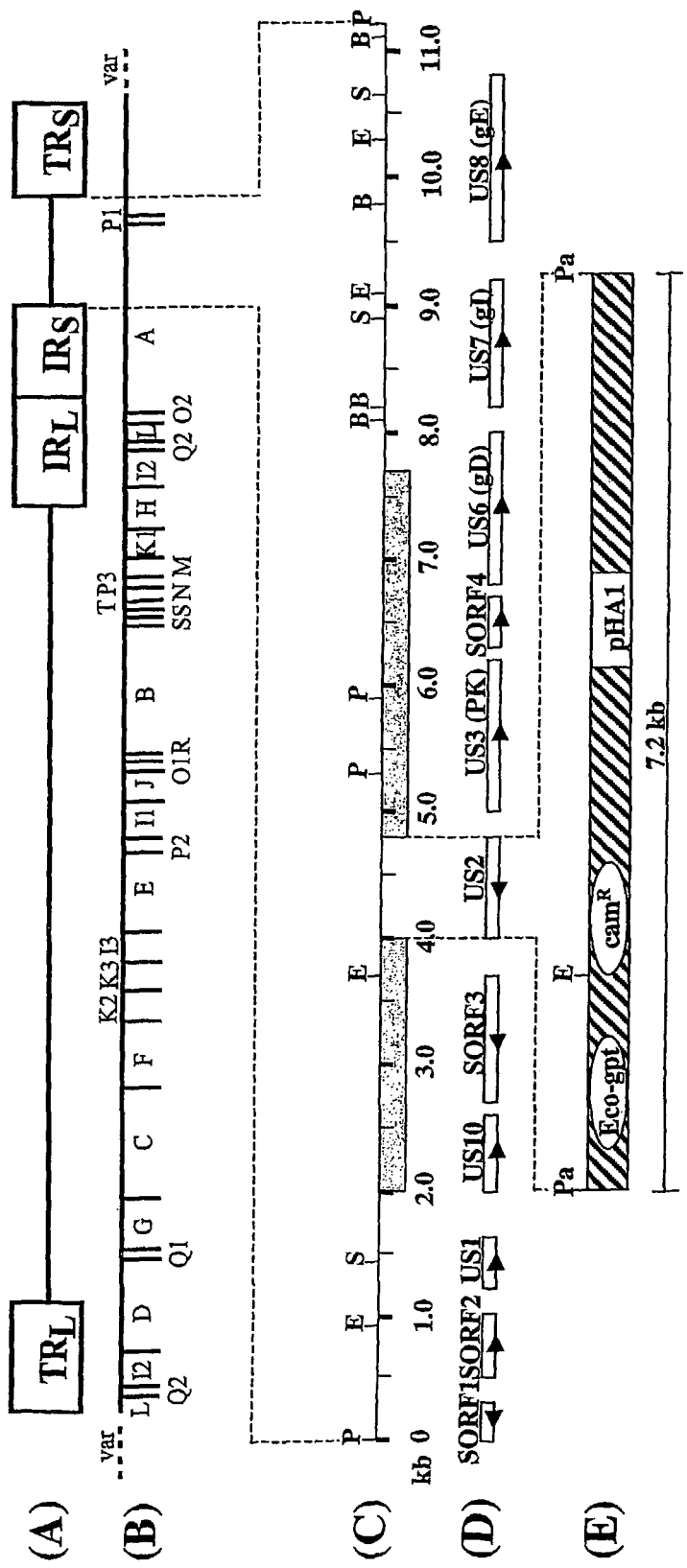

Sonoda et al., Development of an Effective Polyvalent Vaccine against both Marek's and Newcastle Diseases Based on Recombinant Marek's Disease Virus Type I in Commercial Chickens with Maternal Antibodies, Journal of Virology, Apr. 2000, pp. 3217-3226, vol. 74, No. 7.
Ikuta et al., Identification with Monoclonal Antibodies of Glycoproteins of Marek's Disease Virus and Herpesvirus of Turkeys Related to Virus Neutralization, Journal of Virology, Mar. 1984, pp. 1014-1017, vol. 49, No. 3.
Lee et al., Monoclonal Antibodies with Specificity for Three Different Serotypes of Marek's Disease Viruses in Chickens, The Journal of Immunology, Feb. 1983, pp. 1003-1006, vol. 130, No. 2.
Messerle et al., Cloning and mutagenesis of a herpesvirus genome as an infectious bacterial artificial chromosome, Proc. Natl. Acad. Sci., Dec. 1997, pp. 14759-14763, vol. 94.
Morgan et al., Transfection of Chicken Embryo Fibroblasts with Marek's Disease Virus DNA, Avian Diseases, 1990, pp. 3457-3451, vol. 34.
Narayanan, et al., Efficient and precise engineering of a 200 kb β-globin humanlbacterial artificial chromosome in *E. coli* DH10B using an inducible homologous recombination system, Gene Therapy, 1999, pp. 442-447, vol. 6.
Ross et al., Nucleotide Sequence and Characterization of the Marek's Disease Vitus Homologue of Glycoprotein B of Herpes Simplex Virus, J. Gen. Virol. 1989, pp. 1789-1804, vol. 70.
Witter, et al., Increased Virulence of Muck's Disease Virus Field Isolated, Avian Diseases, 1997, pp. 149-163, vol. 41.
Taxonomy Browser, Herpesviridae (Oct. 20, 2006).
Biggs, P.M., Marek's Disease, (K. Hirai ed.), "The History and Biology of Marek's Disease Virus" (Springer, 2001).
Mocarski, Edward S. Jr., Cytomegaloviruses and Their Replication, In Fields B. N., et al., Ed, Virology, 3rd ed., New York, NY, Raven Press, 1996, pp. 2447-2492.
Shizuya et al., Cloning and stable maintenance of 300-kolobase-pair fragments of human DNA in *Escherichia coli* using an F-factor-based vector, Proc. Natl. Acad. Sci. USA, Sep. 1992, pp. 8794-8797, vol. 89.
Suter, Mark et al. BAC-VAC, a novel generation of (DNA) vaccnies: A bacterial artificial chromosome (BAC) containing a replication-competent, packaging-defective virus genome induces protective immunity against herpes simplex virus 1. PNAS 1999, vol. 96 No. 22, pp. 12697-12702.
Schumacher, Daniel et al., Reconstitution of Marek's Disease Virus Serotype-1 (MDV-1) from DNA Cloned as a Bacterial Artificial Chromosome and Characterization of a Glycoprotein B-Negative MDV-1 Mutant: Journal of Virology, 2000, vol. 74 No. 23, pp. 11088-11098.
Becker et al., PCR Detection of Amplified 132 by Repeats in Marek's Disease Virus Type 1 (MDV-1) DNA Can Serve as an Indicator for Critical Genomic Rearrangement Leading to the Attenuation of Virus Virulence, Virus Genes, 1993, pp. 277-87, vol. 7, No. 7, Kluwer Academic Publishers, the Netherlands.
Borst et al., Cloning of the Human Cytomegalovirus (HCMV) Genome as an Infectious Bacterial Artificial Chromosome in *Escherichia coli*: A New Approach for Construction of Hcmv Mutants, Journal of Virology, Oct. 1999, pp. 8320-29, vol. 73, No. 10, American Society for Microbiology.
Brune et al., Rapid identification of essential and nonessential herpesvirus genes by direct transposon mutagenesis, Nature Biotechnology, Apr. 1999, pp. 360-64, vol. 17.
Brune et al., Forward with BACs new tools for herpesvirus genomics, Trends in Genetics, Jun. 2000, pp. 254-59, vol. 16, No. 6.
Cantello et al., Isolation of a Marek's Disease Virus (MDV) Recombinant Containing the lacZ Gene of *Escherichia coli*Stably Inserted within the MDV US2 Gene, Journal of Virology, Mar. 1991, pp. 1584-88, vol. 65, No. 3.
Delecluse et al., Propagation and recovery of intact, infectious Epstein-Barr virus from prokaryotic to human cells, Proc. Natl. Acad. Sci., Jul. 1998, pp. 8245-50, vol. 95, USA.
Fukuchi et al., Map Location of Homologous Regions Between Marek's Disease Virus and Herpesvirus of Turkey and the Absence of Detectable Homology in the Putative Tumor-Inducin Gene Journal of Virology, Mar. 1985, pp. 994-97, vol. 53, No. 3.
Katsuragi-Iwanaga et al., Separation of Marek's Disease Virus DNA by Field Inversion Gel Electrophoresis, Japanese Journal of Veterinary Science, 1990, pp. 1301-04, vol. 52, No. 6.
Bradley et al., Loss of Marek's Disease Virus Tumorigenicity Is Associated with Truncation of RNAs Transcribed within BamHi-H, Journal of Virology, Oct. 1989, pp. 4129-35,. vol. 63, No. 10.
Bradley et al., Structure of the Marek's Disease Virus BamHl-H Gene Family: Genes of Putative Importance for Tumor Induction, Journal of Virology, Jun. 1989, pp. 2534-42, vol. 63, No. 6.
Maotani et al., Amplification of a Tandem Direct Repeat within Inverted Repeats of Marek's Disease Virus DNA during Serial In Vitro Passage, Journal of Virology, May 1986, pp. 657-60, vol. 58, No. 2.
Meindl et al., the Equine Herpesvirus 1 Us2 Homolog Encodes a Nonessential Membrane-Associated Virion Component, Journal of Virology, Apr. 1999, pp. 3430-37, vol. 73, No. 4.
Murphy et al., Virus Taxonomy, Classification and Nomenclature of Viruses, 1995, 3 pages.
Osterrieder, N., Sequence and initial characterization of the UL10 (glycoprotein M) and UL11 homologous genes of serotype 1 Marek's Disease Virus, Arch. Virol., 1999, pp. 1853-63, vol. 144.
Schat et al., Open reading frame L1 of Marek's disease herpesvirus is not essential for in vitro and in vivo virus replication and establishment of latency, Journal of General Virology, 1998, pp. 841-49, vol. 79, Great Britain.
Schat et al., Marek's Disease, 1985, 11 pages, Kluwer Academic Publishers.
Zhang et al., A new logic for Dna engineering using recombination in *Escherichia coli*, Nature Genetics, Oct. 1998, pp. 123-28, vol. 20.
Brunovskis et al., the Marek's Disease Virus (MDV) Unique Short Region: Alphaherpesvirus-Homologous, Fowlpox Virus-Homologous, and MDV-Specific Genes, Virology, 1995, pp. 324-38, vol. 206.
Smith et al., A self-recombining bacterial artificial chromosome and its application for analysis of herpesvirus pathogenesis, PNAS, Apr. 25, 2000, pp. 4873-78, vol. 97, No. 9.
Cui et al., Marek's Disease Virus Gene Clones Encoding Virus-Specific Phosphorylated Polypeptides and Serological Characterization of Fusion Proteins, Virus Genes, 1990, pp. 309-22, vol. 3, No. 4.
Fukuchi et al., Structure of Marek's Disease Virus DNA: Detailed Restriction Enzyme Map, Journal of Virology, Jul. 1984, pp. 102-09, vol. 51, No. 1.
Muyrers et al., Rapid modification of bacterial artificial chromosomes by ET-recombination, Nucleic Acids Research, 1999, pp. 1555-57, vol. 27, No. 6.
Osterrieder et al., The equine herpesvirus 1 glycoprotein gp21/22a, the herpes simplex virus type 1 gM homolog, is involved nvolved in virus penetration and cell-to-cell spread of virions, Journal of Virology, 1996, pp. 4110-15, vol. 70, No. 6.
Parcells et al., Retention of Oncogenicity by a Marek's Disease Virus Mutant Lacking Six Unique Short Region Genes, Journal of Virology, Dec. 1995, pp. 7888-98, vol. 69, No. 12.
Parcells et al., Characterization of a Marek's Disease Virus Mutant Containing a LacZ Insertion in the US6 (gD) Homologue Gene, Virus Genes, 1994, pp. 5-13, vol. 9, No. 1.
Ross et al., DNA sequence and organization of genes in a 5.5 kbp EcoRI fragment mapping in the short unique segment of Marek's disease virus (strain RB1B), Journal of General Virology, 1991, pp. 949-54, vol. 72.
Witter et al, Marek's Disease, 1985, 11 pages, Kluwer Academic Publishers.
Witter, R., Very virulent Marek's disease viruses: importance and control, World's Poultry Science Journal, Mar. 1989, pp. 60-65, vol. 45.
Payne et al, Marek's Disease, 1985, 11 pages, Kluwer Academic Publishers.

(56) References Cited

OTHER PUBLICATIONS

Wagner et al., Systematic Excision of Vector Sequences from the Bac-Cloned Herpesvirus Genome during Virus Reconstitution, Journal of Virology, Aug. 1999, pp. 7056-60, vol. 73, No. 8.

Parcells et al., Characterization of Marek's Disease Virus insertion and Deletion Mutants That Lack US1 (ICP22 Homolog), US10, and/or US2 and Neighboring Short-Component Open Reading Frames, Journal of Virology, Dec. 1994, pp. 8239-53, vol. 68, No. 12.

Sambrook et al., Molecular Cloning, A Laboratory Manual, Second Edition, 1989, 31 pages.

Smith et al., Construction and Transposon Mutagenesis in *Escherichia coli* of a Full-Length Infectious Clone of Pseudorabies Virus, an Alphaherpesvirus, Aug. 1999, pp. 6405-14, vol. 73, No. 8.

Silva et al., Genomic Expansion of Marek's Disease Virus DNA Is Associated with Serial In Vitro Passage, Journal of Virology, Jun. 1985, pp. 690-96, vol. 54, No. 3.

Van Iddekinge et al., Genome Analysis of Marek's Disease Virus Strain CVI-988: Effect of Cell Culture Passage on the Inverted Repeat Regions, Jun. 1999, pp. 182-88, vol. 43, No. 2.

Warden, et. al., Herpesvirus BACs: Past, Present and Future, Journal of Biomedicine and Biotechnology, Article ID 124595, vol. 2011, pp. 1-16 (2011).

Nagaike, et. al., Cloning of the Varicella-Zoster Virus Genome As an Infectious Bacterial Artificial Chromosome in *Escherichia Coli*, Vaccine, vol. 22, pp. 4069-4074 (2004).

* cited by examiner

SEQUENCE LISTING

<160> NUMBER OF SEQ ID NOS: 8

<210> SEQ ID NO 1
<211> LENGTH: 25
<212> TYPE: DNA
<213> ORGANISM: Artificial sequence
<220> FEATURE:
<223> OTHER INFORMATION: Synthesized sequence, primer MUS21

<400> SEQUENCE: 1
acaggattcc gtgtttgaat actgg                                          25

<210> SEQ ID NO 2
<211> LENGTH: 33
<212> TYPE: DNA
<213> ORGANISM: Artificial sequence
<220> FEATURE:
<223> OTHER INFORMATION: Synthesized sequence, primer MUS22

<400> SEQUENCE: 2
atagtcgact ttaattaacc ggtagtcatt agc                                 33

<210> SEQ ID NO 3
<211> LENGTH: 36
<212> TYPE: DNA
<213> ORGANISM: Artificial sequence
<220> FEATURE:
<223> OTHER INFORMATION: Synthesized sequence, primer MUS23

<400> SEQUENCE: 3
atcgcatgct taattaattt ggcaaaacgg aatagg                              36

<210> SEQ ID NO 4
<211> LENGTH: 35
<212> TYPE: DNA
<213> ORGANISM: Artificial sequence
<220> FEATURE:
<223> OTHER INFORMATION: Synthesized sequence, primer MUS24

<400> SEQUENCE: 4
cgcaagctta atatgaatct ctaaaacttc tcggc                               35

<210> SEQ ID NO 5
<211> LENGTH: 28

```
<212> TYPE: DNA
<213> ORGANISM: Artificial sequence
<220> FEATURE:
<223> OTHER INFORMATION: Synthesized sequence, primer gB-up

<400> SEQUENCE: 5
gatagaatcc atgcactatt ttaggcgg                                          28

<210> SEQ ID NO 6
<211> LENGTH: 30
<212> TYPE: DNA
<213> ORGANISM: Artificial sequence
<220> FEATURE:
<223> OTHER INFORMATION: Synthesized sequence, primer gB-low

<400> SEQUENCE: 6
atacctcgag ttacacagca tcatcttctg                                        30

<210> SEQ ID NO 7
<211> LENGTH: 80
<212> TYPE: DNA
<213> ORGANISM: Artificial sequence
<220> FEATURE:
<223> OTHER INFORMATION: Synthesized sequence, primer gBkana

<400> SEQUENCE: 7
ttttctttca tcaatagatg ttcgttccaa atcatctgat tcctcgccat aaagcactaa       60
atcggaaccc taaagggagc                                                   80

<210> SEQ ID NO 8
<211> LENGTH: 80
<212> TYPE: DNA
<213> ORGANISM: Artificial sequence
<220> FEATURE:
<223> OTHER INFORMATION: Synthesized sequence, primer gBkanb

<400> SEQUENCE: 8
atatagacag atcactaatc gatatacaga taggacgccc gtttccattg attgtctcct       60
tccgtgtttc agttagcctc                                                   80
```

VACCINATION AGAINST HOST CELL-ASSOCIATED HERPES VIRUSES

CROSS-REFERENCE TO RELATED APPLICATION

This application is a continuation of PCT International Patent Application No. PCT/EP/01/08893, filed on Aug. 1, 2001, designating the United States of America, and published, in English, as PCT International Publication No. WO 02/12288 A3 on Feb. 14, 2002, the contents of the entirety of which is incorporated herein by this reference.

TECHNICAL FIELD

The invention relates to the field of vaccination against so-called host cell-associated herpes viruses such as Marek's disease virus (MDV) of poultry and Varicella Zoster Virus (VZV, causing chickenpox and zoster after reactivation from latency) of man and to vaccination against disease caused by these viruses, and, in particular, relates to poultry disease, in particular to the field of vaccination against Marek's disease.

BACKGROUND

In particular, Marek's disease has been a problem of the poultry industry from the beginning of intensive production of poultry meat. It is a herpes viral disease that is causing a large variety of clinical signs starting from immunosuppression, neurological disorders, anemia and unspecified apathies and ending with severe lymphatic cancers at later stages of infection. In the beginning of the history of Marek's disease, there were no treatments and no preventive measures. Then an apathogenic-related (Serotype 3) virus was isolated from turkeys (HVT) and was initially used for vaccination.

However, some time after introduction of vaccination with HVT, Marek's disease emerged again and it became clear that the circulating field viruses had changed to circumvent the protection induced by the HVT strain. At this time, a new apathogenic virus was discovered (Rispens strain), which in general has the same serotype as the viruses causing disease. This vaccine strain was introduced very rapidly into the market and produced very good vaccination results.

However, again, after about ten years, new outbreaks of disease occurred; again, circulating field viruses had changed to circumvent the protection induced by the vaccine strain in current use. Then a combination of both vaccines (HVT and Rispens) was used to protect the animals; however, satisfactory results were only seen temporarily. Currently, new outbreaks of disease occur despite all these vaccinations. The reason for this is not yet understood but there is a clear need for the introduction of new potent vaccines.

Problems associated with vaccinations against Marek's disease are that, despite the fact that Marek vaccines have been produced for a long period, the method of preparation of the vaccines could not be improved. The reason for this is that, in general, the essentially host cell-associated virus can be grown essentially only in primary host cells such as in the case of MDV or HVT in primary cells such as fibroblasts prepared from poultry, such as chickens, free of pathogens and, in the case of Varicella Zoster Virus, in (essentially primary) human cells (again, of course, free of contaminating pathogens) and cannot or only with great difficulties be achieved out of context of the specific cell of the respective host. This makes, in general, a vaccine directed against viral infections or disease caused by these types of viruses difficult, if not nearly impossible on a practical level, to produce and thus expensive.

For example, the Rispens vaccine directed against Marek's disease, which is at present considered the only sufficiently potent one, is, as all serotype-1 Marek viruses, strictly host-cell associated. Infectivity of the cell-associated virus (such as, for example, serotype 1 and 2) is completely lost during normal freezing or lyophilization. Therefore, the preparation of the vaccine includes a very complicated and expensive step, where whole cells must be frozen in liquid nitrogen. The vaccine must be stored and transported and kept under liquid nitrogen until use and therefore causes tremendous costs and problems during transport.

Then, at the site of use, the vaccine must be used very carefully, since the infected cells are very sensitive to environmental factors. Factors such as elevated temperatures, exposure to light and residual detergents in glassware used often damage the virus such that no sufficiently viable vaccine batch can be prepared, leading to complete vaccine failures. Such failures can be recognized only when the disease already starts to break out and the affected poultry show symptoms of disease.

In short, up to now, all attempts to provide inactivated, subunit or recombinant vaccines to protect against Marek's disease failed and, therefore, there is currently no alternative to live, cell-associated vaccines comprising Marek's Disease Virus. Marek's disease remains to be controlled by application of infected-cell preparations as a vaccine. These preparations not only contain living cells suspended in DMSO-containing media and the whole variety of cellular antigens, but they also have to be stored in liquid nitrogen. Consequently, the cold chain has to be maintained from vaccine production to the vaccine user and until administration. In addition, once thawed, the vaccine has to be administered within a very short period of time and every bird has to be injected. Several of these problems are shared by those wishing to prepare vaccines against other essentially cell-associated herpes viruses such as Varicella Zoster Virus.

Marek's disease virus (MDV) is a member of the Alpha-herpesvirinae subfamily of the Herpesviridae (Lee et al., 2000; Murphy et al., 1995). Based on virulence for the chicken and ability to induce T cell lymphomas, MDV is generally grouped into three serotypes (MDV-1, MDV-2, and MDV-3). MDV-3 represents the herpes virus of turkeys (HVT) which was widely used for vaccination against MDV-related disease. However, after vaccination failures and development of so-called virulent or very virulent MDV-1 (Witter, 1985), attenuated MDV-2 strains and later attenuated MDV-1 strains (e.g., strain CVI 988 Rispens) were used in vaccine formulations (Witter, 1985). In recent years and first reported in the United States, even more virulent MDV-1, so-called very virulent plus (vv+), and MDV-1 variants appeared and caused high incidence of Marek's disease and mortality caused by tumor development and immunosuppression early after infection (Witter, 1997). One vv+ strain, 584A, was passaged more than 100 times on chicken embryo fibroblasts (CEF) and was shown to loose pathogenicity for chickens (Witter, 1997). However, the molecular basis for the increased pathogenicity of vv+ MDV-1 and similarly for loss of virulence are poorly understood because molecular analyses of MDV-1 are difficult to perform. On the one hand, no or only small amounts of infectious virus progeny is released in cultured cells; on the other hand, production of MDV-1 recombinants is laborious and, due to the highly cell-associated nature of the agent in cell culture, multiple rounds of purification of virus recombinants are needed (Cantello et al., 1991; Sakaguchi et al., 1993; Parcells et al., 1994; Schat et al., 1998; Anderson et al., 1998).

On top of that, as mentioned already above, vaccination cannot guarantee to protect the animals from all Marek's disease field viruses. The virus—as all Herpes viruses—is capable of finding ways to escape the immune response induced by the vaccines. Therefore, rapid adaptation of vaccines to the field situation would be needed. Currently, this is done by isolation of field isolates (such as HVT or Rispens) and/or further attenuation in vitro. The isolation itself is causing tremendous problems because of the difficulties of getting the cell-associated infectious virus out of chickens and infecting cells in cell culture. The attenuation steps that would follow are very laborious and time consuming, especially since plaque purification is extremely difficult, which is again due to the cell-associated nature of the virus.

The result from attenuation is normally not defined. As a result of these facts, no vaccines that would provide relief where current HVT- and Rispens-type vaccines fail have entered the market for a long time. In addition, often an over-attenuation occurs during vaccine production since the virus has been passaged for too many times. This further aggravates the low efficacy of the HVT- and Rispens-type vaccines in the field. In short, the following problems constitute a large part of the current impasse in MDV control. There is a low reproducibility of classical vaccine production; one sees over-attenuation of vaccine virus, undefined attenuation of vaccine virus, high production costs, high storage and transport costs, high sensitivity of the vaccine to environmental factors, and a too slow development of new vaccine strains especially for cell associated viruses.

These problems are compounded by the fact that now circulating field viruses give rise to high antibody titers in poultry production stock, whereby these high antibody titers are given through the progeny via maternal antibody in the eggs. The influence of these maternal antibodies during initial infection by current vaccine virus further decreases the current efficacy of vaccination against Marek's disease.

DISCLOSURE OF THE INVENTION

The invention provides a vaccine directed against an infection caused by a herpes virus that is essentially host-cell associated comprising a recombinant viral genome derived from the herpes virus, the genome allowing recombination essentially free of the host cell. To that effect, the invention herewith provides a recombinant viral genome derived from a herpes virus that is considered to be essentially host cell associated, the genome preferably capable of at least some measure of replication in the host cell and at the same time allowing recombination essentially free or independently of the host cell. Homologous recombination in eukaryotic cells is no longer required. In the detailed description, such a genome is provided for a Marek's disease-like virus.

Therein, as an example, a genome of Marek's disease virus serotype 1 (MDV-1), strain 584Ap80C, was cloned in *Escherichia coli* as a bacterial artificial chromosome (BAC). BAC vector sequences were introduced into the Us2 locus of the MDV-1 genome by homologous recombination after co-transfection of chicken embryo fibroblasts (CEF) with viral DNA and recombinant plasmid pDS-pHA1 which contained BAC sequences and the Eco-gpt gene instead of the MDV-1 Us2 gene and flanking sequences. Transfection progeny was passaged on CEF cells in the presence of mycophenolic acid and xanthine/hypoxanthine. After four rounds of selection, viral DNA was prepared and used to transform *Escherichia coli* strain DH10B. Several colonies harboring the complete MDV-1 genome were identified. These MDV-1 BACs were transfected into CEF cells and from 3 days after transfection, infectious MDV-1 was recovered. Growth of MDV-1 recovered from various BACs was indistinguishable of that of the parental virus as assayed by plaque formation and determination of growth curves.

The invention thus provides a method for producing or obtaining a recombinant essentially host-cell associated herpes viral genome comprising (if required near complete or complete) infectious herpes viral nucleic acid derived from an MDV and/or VZV isolate.

Now that the essentially complete genome is obtained free of the host cells, it was originally thought to be firmly associated. The invention also provides a genome that allows full application of all recombinant techniques available to the person skilled in the art of molecular biology and, for example, thus also provides a vaccine at least comprising a (replicative) minigenome.

For example, the invention provides a minigenome that provides for the expression of only a couple of glycoproteins (such as gB, gC, gD or combinations thereof) and, for example, ICP4 or another gene product that has been shown to induce cellular immunity in herpes viruses. Such a minigenome serves to identify genes that are important in protection, considering that replication of the genome in (eukaryotic) host cells is no longer provided. Adding, for example, a HCMV or SV40 promoter in front of each gene or gene construct would provide for the final identification of a minimal protective unit. For a replication-competent minigenome, the invention also provides deleting the entire US region, or a major part thereof, whereby the resulting minivirus replicates also in host cells.

In another embodiment, the invention provides such a genome which comprises an essentially full-length copy derived from the herpes virus, "essentially full-length" herein indicating that a great part of the genes of the viral genome is present, except for some that are preferably (at least functionally) left out such as a gene essential for replication or spread of the virus in a host or host cell culture, as provided herein in the detailed description. For example, in one of the recovered genomes according to the invention, BAC20, sequences encoding glycoprotein B (gB) were deleted by one-step rece-mediated mutagenesis using a linear DNA fragment. Glycoprotein B-negative MDV-1 reconstituted after transfection of gB-negative BAC20 DNA (20DgB) were only able to grow on cells providing gB in trans, demonstrating that gB is essential for MDV-1 growth in cultured host cells. Other genes essential for growth and for which cells can be provided which produce the gene product in trans are gH, ICP4, UL15, UL28 and UL9, or other genes considered essential for growth such as those listed below.

Furthermore, the invention provides use of a genome for the preparation of a vaccine. In one embodiment, such a vaccine is directed against a disease caused by an infection with an essentially host cell-associated herpes virus; however, in another embodiment, such a vaccine may be used as a vector vaccine and may comprise other or additional pathogens or nucleic acid stretches encoding therefor. For MDV, preferred additional pathogen nucleic acid comprises nucleic acid derived from, for example, Newcastle Disease virus, Eimeria spp, Salmonella spp, chicken infectious anemia virus, influenza virus, infectious bursal disease virus, reovirus, or other pathogens commonly seen in poultry.

Thus, the invention also provides a vaccine wherein the genome comprises a functional deletion in a gene essential for replication and/or spread of the herpes virus in a host cell, or wherein the viral genome at least comprises a nucleic acid encoding an antigenic substance capable of eliciting an (preferably essentially protective) immune response against an infection of an individual with the herpes virus. A typical essential gene or fragment thereof to be deleted can, for example, be an MDV homologue of UL1=glycoprotein L; UL5; UL8; UL9; UL15; UL18; UL19; UL22=glycoprotein H; UL26; UL26.5; UL27=glycoprotein B; UL28; UL29; UL30; UL52; UL53; ICP4 or genes or fragments thereof selected from the US region of the genome (FIG. 1).

In a preferred embodiment, the invention provides a vaccine comprising a functional deletion in a gene essential for eliciting a marker immune response specific for the herpes virus allowing immunological discrimination between an individual vaccinated with the vaccine and an individual infected with the essentially cell associated herpes virus. Preferred marker responses are, for example, directed at gC, gM, gD, or gE, whereby the detailed description further explains (here in the case of gM) such a deletion in a gene essential for eliciting a marker immune response.

Furthermore, the invention provides a vaccine wherein the viral genome at least comprises a nucleic acid encoding a proteinaceous substance capable of modulating transcription and/or translation of a nucleic acid encoding an antigenic substance capable of eliciting an immune response against an infection of an individual with the herpes virus.

Preferably, the vaccine comprises an essentially full-length copy derived from the herpes virus to maintain as many functions required for effective modulation of transcription and/or translation of the vaccine genome in the vaccinated host; however, minigenomic vaccination is also provided herein. It is, of course, preferred to efficiently modulate transcription and/or translation of a nucleic acid encoding a foreign pathogen, or antigenic substance derived thereof, when expressing an additional pathogen or an antigenic substance derived thereof from the genome, and it may be contemplated that also foreign pathogens (i.e., non-herpes virus regulatory elements) are provided to the genome when providing a vaccine according to the invention provided with a nucleic acid encoding an additional pathogen.

In particular, the invention provides a vaccine wherein the herpes virus comprises Marek's disease-like virus. In particular, is it preferred to provide a vaccine wherein the Marek's disease-like virus comprises serotype 1. Also, now that methods for manipulation of the genome involved beyond the context of the host cell with which the genome originally was associated are provided, a vaccine is provided that, instead of being derived from normal attenuated or a-virulent isolates of Marek's disease-like virus, is derived instead from a virulent, a very virulent or a very virulent plus field-virus, because rapid isolation of infectious clones from field isolates is now possible, allowing preparation of DNA vaccines for prevention of Marek's disease in chicken and turkeys, where mutations into the genome can be introduced very rapidly. The same system can be used also for other essentially cell-associated Herpes viruses like Varicella Zoster Virus.

The use of replicative viral genomes as provided herein containing parts of or entire and infectious Marek's Disease virus (MDV-1) genomes opens a variety of new possibilities to generate more efficacious, biologically safe and stable MDV-1 vaccines. Owing to the fact that recombinant MDV-1 are recovered from cloned DNA, virus progeny resulting from DNA transfections can be better characterized and "over-attenuation" of vaccine viruses can be avoided. For example, the number of 132-bp repeats which appears to be associated with attenuation (Maotani et al., 1986) can be exactly determined and, if necessary, be reduced or enlarged according to the needs for vaccine production or the situation in the field (see further herein). The generation of mutant MDV-1 is greatly facilitated. So far, MDV-1 mutants are generated by laborious and time-consuming homologous recombination and selection procedures in eukaryotic cells. These selection procedures—as reported for other herpes viruses—often result in mutations of the genome other than those desired, especially since in the case of MDV-1, no cell-free virus can be obtained which makes selection procedures and recovery and propagation of mutants even more complicated. In contrast, the invention provides a method to manipulate a viral genome based on mutagenesis via a recE, recT and the recB/C-suppressing λ gam gene present on plasmid pGETrec (Narayanan et al., 1999). The advantages of the system are (i) that only 30 to 50 bp homology arms are needed to target a specific sequence to be deleted, i.e., deletion of any open reading frame can be achieved without the need to clone recombination cassettes, (ii) the method is very fast, and (iii) the pGETrec vector conferring the mutagenesis system and expressing ampicillin resistance is rapidly lost from bacterial cells in the absence of ampicillin.

By using the powerful techniques using the so-called E/T cloning procedures, one-step mutation and selection in *Escherichia coli* is possible (Muyrers et al., 1999; Narayanan et al., 1999; Zhang et al., 1998). This technique also allows the deletion of essential MDV-1 genes without the need of using complementing cell lines since replication of mutated MDV-1 genomes as provided herein does not require the transcomplementation of the essential gene deleted. In addition, cloning procedures are completely unnecessary.

In another embodiment, the invention provides a method of generating MDV-1 or other (essentially cell-associated herpes) virus BACs, comprising transforming, for example, *Escherichia coli* DH10B cells with plasmid pBADαβγ, pGETrec or any other plasmid that inducibly or stably expresses recE, recT and the λ gam gene, followed by preparing circular viral DNA from lytically or latently infected cells taken, for example, ex vivo or from cell cultures. In a parallel or separate procedure, linear DNA harboring BAC vector sequences and sequences that allow homologous recombination of the BAC vector sequences with the viral DNA are provided. This linear DNA can, e.g., be produced by PCR or by linearizing plasmid DNA. Then, expression of recE, recT and the gam gene in the *Escherichia coli* is provided and electrocompetent cells are provided (e.g., Sambrook et al., 1989). Viral DNA is then electroporated together with linear DNA harboring the BAC vector sequences into competent *Escherichia coli*. Plating on agar containing appropriate antibiotics provides for the to-be-harvested colony or colonies and BAC DNA can be prepared as, for example, described in the detailed description herein. Infectivity of cloned viral BAC DNA is checked by transfection of susceptible cells. Herewith, the invention provides a method to genetically recombine an essentially host cell-associated herpes viral genome derived from a host cell or tissue without the need to perform (homologous) recombination in eukaryotic cells, allowing one to obtain an (if required near complete or complete) infectious genome or herpes viral nucleic acid derived from field isolates or attenuated isolates alike.

The method as provided herein will also allow one to further attenuate candidate vaccine MDV-1 or to generate MDV-1 mutants harboring genes of other important chicken pathogens. In addition, emerging field MDV-1 isolates with possibly different and changing antigenetic properties can be countered by providing a vaccine based on exchange of the respective mutated genes between the cloned MDV-1 and the current field isolate(s). These changes—as described above—can be performed with the same E/T cloning technique and, as such, provide the possibility to react to changes of MDV-1 in the field very rapidly. An attractive advantage of a recovery of infectious MDV-1 as described herein, however, is the use of a genome as provided herein as DNA vaccine. Up to now, Marek's disease is controlled by application of infected-cell preparations.

These preparations not only contain living cells suspended in DMSO-containing media and the whole variety of cellular antigens, but they also have to be stored in liquid nitrogen. Consequently, the cold chain has to be maintained from vaccine production to the vaccine user and until administration. In addition, once thawed, the vaccine has to be administered within a very short period of time and every bird has to be injected. With MDV-1 genome DNA as provide herein, purification of the "vaccine" (DNA) is easily feasible and reproducible. DNA is extremely stable, the maintenance of the cold chain is not necessary, and infectious DNA can be administered by several routes (intramuscularly, intradermally, in-ovo, orally, by the respiratory route, and so on) and in different formulations (with and without a carrier, etc.). In addition, the presence of maternal antibodies does not interfere with primary injection of the immunogen.

As such, MDV-1 genomes as herein provided allow for the first time the possibility to produce and engineer highly efficient and biologically safe vaccines against a tumorigenic and economically important disease. The invention thus in general provides a method for limiting the risks of an individual on acquiring or fully manifesting a disease caused by an infection with an essentially host cell-associated herpes virus comprising administering to the individual a vaccine according to the invention or a genome according to the invention.

BRIEF DESCRIPTION OF FIGURES

FIG. 1 Schematic illustration of the cloning procedure to generate BACs harboring complete MDV-1 genomes. Shown is the organization of the approximately 180 kbp MDV-1 genome (A) and the BamHI-restriction map (B) according to Fukuchi et al. (11). The unique short region (Us) and the ORFs located in the Us are shown (C and D). A 2.1 and a 3.1 kbp fragment bordering the Us2 gene (grey boxes) were amplified by PCR and cloned into plasmid pTZ18R to give rise to recombinant plasmid pDS. The 7.2 kbp BAC vector released from recombinant plasmid pHA1 (15) was inserted into pDS, resulting in plasmid pDS-pHA1 (E). Restriction enzyme sites according to (2) are abbreviated: B=BamHI, E=EcoRI, P=PstI, Pa=PacI, S=SalI.

FIG. 2 Digitally scanned image of an ethidium bromide stained 0.8% agarose gel. DNA isolated from *E. coli* DH10B clones BAC19, BAC20 and BAC24 was cleaved with BamHI or EcoRI and separated. The restriction enzyme digests are flanked by the 1 kb ladder (Gibco-BRL). Asterisks indicate additional bands or size variations of individual fragments between the three BAC clones.

FIG. 3 Digitally scanned image of DNA of 584Ap80C (V), BAC19, BAC20 and BAC24 cleaved with BamHI or EcoRI, separated by 0.8% agarose gel electrophoresis and stained with ethidium bromide (left panel). After Southern transfer of DNA fragments to Nylon membranes, hybridization with Digoxigenin-labeled fragments released from plasmid pDS or pHA1 was performed. Size markers (1 kb ladder, Gibco-BRL) and sizes of reactive bands are given.

FIG. 4 Digitally scanned images of Southern blots to analyze size variations in BAC19, BAC20 and BAC24 DNA. Viral DNA of strain 584Ap80C (V) and individual BACs was cleaved with BamHI or EcoRI and transferred to Nylon membranes. Sheets were incubated with Digoxigenin-labeled BAC19 DNA or labeled BamHI-C or BamHI-D fragments. Size markers (1 kb ladder, Gibco-BRL) are given. The smear-like appearance of bands in the case of 584Ap80C DNA when hybridized with BamHI-D sequences is indicated by brackets.

FIG. 5 (A) IIF analysis of MDV-1 plaques after transfection of BAC19, BAC20 or BAC24 DNA. At 5 days after transfection, infected cells were fixed and subjected to indirect immunofluorescence using anti-gB mab 2K11. Detection of bound antibodies was performed with anti-mouse ALEXA™ 488 dye conjugates (Molecular Probes) and nuclei were counterstained with propidium iodide. Magnification=400×.

(B) Growth curves of MDV-1 strain 584A and various BACs. After infection of CEF cell with 100 p.f.u. of 584Ap80C or transfection progeny of BAC19, BAC20 or BAC24, virus titers were determined at the indicated times p.i. by co-seeding with fresh CEF cells. Plaques were counted after immunofluorescent staining with mab 2K11.

FIG. 6 Digitally scanned images of Southern blots to analyze the stability of BAC vetor sequences in viruses recovered after transfection of BAC19 and BAC20. Transactions progeny was passaged for four times and after each passage, viral DNA was isolated. Virus DNA was cleaved with BamHI or EcoRI, separated by 0.8% agarose gel electrophoresis and transferred to Nylon membranes. Southern blot hybridization was performed using Digoxigenin-labeled fragments of plasmids pDS or pHA1. Abbreviations: V=584Ap80C, 19=BAC19, 20=BAC20. Passages 1 to 4 after transfection of BAC19 DNA are indicated by numbers 1 to 4. Passage 4 after transfection of BAC20 DNA was loaded in the last lane, respectively, and is indicated by 4a. Sizes of reactive fragments are given. Asterisks indicate the reactive 1.6 kb band of the marker (1 kb ladder, Gibco-BRL).

FIG. 7 (A) Schematic illustration of mutagenesis of BAC20 to remove gB-encoding sequences. Recombinant plasmid pGETrec encoding L-arabinose-inducible recE, recT, and gam gene was transformed into BAC20-containing DH10B cells. After PCR amplification of the kan$^R$ gene from plasmid pEGFP-N1 (Clontech) with primers that also contained 50 nt homology arms bordering the gB deletion, a 1.6 kbp PCR amplicon was electroporated into DH10B cells harboring BAC20 and pGETrec. Bacterial suspensions were plated on agar containing 30 μg/ml kanamycin and 30 μg/ml chloramphenicol. Double-resistant colonies were picked and subjected to further analysis.

(B) Schematic illustration of the location of the gB gene in MDV-1 and the deletion present in BAC 20DgB.

FIG. 8 Scanned image of an ethidium bromide stained 0.8% agarose gel containing BAC20 and 20DgB DNA cleaved with BamHI, EcoRI, BglI, or StuI and separated by 0.8% agarose gel electrophoresis (left panel). DNA fragments were transferred to nylon membranes and hybridized with a Digoxigenin-labeled kan$^{R-}$ gB-specific probe. Sizes of reactive DNA fragments are indicated. Abbreviations: B=BamHI, E=EcoRI, Bg=BglI, S=StuI.

FIG. 9 Confocal laser scan analysis of MgB1 cells constitutively expressing MDV-1 gB. MgB1 or QM7 cells were seeded on glass cover slips and incubated with anti-gB mab 2K11 or convalescent chicken serum MDSI. Secondary antibodies were anti-mouse or anti-chicken IgG ALEXA™ 488 dye conjugates (Molecular Probes). Nuclei were counterstained with propidium iodide. Bar represents 10 μm.

FIG. 10 IIF analysis of MgB1, QM7 or CEF cells after transfection with BAC20 (upper panels) or 20DgB (lower panels). At 5 days after transfection, cells were fixed with acetone and incubated with anti-pp38 mab H19. The secondary antibody was anti-mouse IgG ALEXA™ 488 dye conjugates. Whereas MDV-1 plaques were observed on all cell lines after transfection of BAC20 DNA, viral plaques were only observed on MgB1 cells after transfection with 20DgB. Only single infected cells were observed on QM7 and CEF cells (arrowheads). Magnification=400 ×.

DETAILED DESCRIPTION OF THE INVENTION

Marek's disease virus (MDV) is a member of the Alphaherpesvirinae subfamily of the Herpesviridae (van Regenmortel et al., 1999). Based on virulence for chickens, the ability to induce T cell lymphomas and antigenic properties, MDV is grouped into three serotypes (MDV-1, MDV-2, and MDV-3) (Payne, 1985). MDV-3 represents the herpes virus of turkeys (HVT) which has been widely used for vaccination against MDV-related disease. According to the most recent nomenclature, MDV-1 is classified as gallid herpes virus 2 (GHV-2), MDV-2 as GHV-3, and HVT as meleagrid herpes virus. All three viruses belong to the new Marek's disease-like virus genus within the Alphaherpesvirinae.

Control of MDV-1 infection was achieved by vaccination primarily with HVT; however, after vaccination failures and description of so-called "very virulent" MDV-1 (Witter, 1989), MDV-2 strains and later attenuated MDV-1 strains (e.g., strain CVI 988 Rispens) have been used in vaccine formulations (Witter, 1985).

In recent years and first reported in the United States, even more virulent MDV-1, "very virulent plus" (vv+), and MDV-1 variants appeared and caused high mortality even in vaccinated flocks (Witter, 1997). One of these vv+ strains, 584A, was passaged serially on chicken embryo fibroblasts (CEF) and lost pathogenicity for chickens (Witter, 1997). The molecular basis for the increased pathogenicity of vv+ MDV-1 and similarly for loss of virulence are poorly understood because molecular analyses of MDV-1 are difficult to perform.

On the one hand, no infectious virus progeny is released in cultured cells; on the other hand, production of MDV-1 recombinants is laborious and, due to the highly cell-associated nature of the agent in vitro, multiple rounds of purification of virus recombinants are needed (Cantello et al., 1991; Sakaguchi et al., 1993; Parcells et al., 1994, 1995; Schat et al., 1998; Anderson et al., 1998). In addition, primary cells have to be used for growth of MDV-1 (Payne), resulting in the fact that analysis of essential MDV-1 genes is almost impossible because no transcomplementing cell lines can be generated.

The genomes of murine and human cytomegaloviruses (MCMV and HCMV; Messerle et al., 1997; Borst et al., 1999), herpes simplex virus type 1 (HSV-1; Suter et al., 1999), pseudorabies virus (PrV; Smith et al., 1999, 2000), and Epstein-Barr virus (EBV; Delecluse et al., 1998) have been cloned as infectious BACs using this technique.

The aim of this study was to provide a basis for fast and efficient production of MDV-1 recombinants by cloning of the complete 180 kbp genome in *Escherichia coli*. Infectious MDV-1 was readily recovered after transfection of cloned MDV-1 BAC DNA using CEF cells and MDV-1 BACs were stable after several rounds of bacterial growth or serial propagation in CEF cells.

Lastly, because one-step deletion of an essential MDV-1 gene in *Escherichia coli* was possible, the system may have great potential to facilitate future analysis of essential and nonessential MDV-1 genes and serve as a tool for production of biologically safe modified live virus and/or DNA vaccines.

The invention is further explained with the aid of the following illustrative examples.

EXAMPLES

Materials and Methods

Virus and cells. Primary or secondary chicken embryo fibroblasts (CEF) or quail muscle (QM7) cells were maintained in Dulbecco's modified essential medium (DMEM) supplemented with 5 to 10% fetal calf serum (FCS). MDV-1 strain 584Ap80C was kindly provided by Dr. Richard Witter, ADOL, East Lansing, Mich., U.S.A. Strain 584Ap80C represents an avirulent cell culture passaged descendant of vv+ strain 584A (Witter, 1997) and was grown on primary or secondary CEF cells as previously described (Osterrieder, 1999). QM7 cells were tested for the absence of MDV-1 sequences by PCR and Southern blot hybridization targeting different regions of the genome before they were used for propagation of MDV-1 (Tischer, 2002). Virus growth curves were done as described with slight modifications (Parcells et al., 1994). Briefly, 100 plaque-forming units (p.f.u.) were used to infect $2\times10^6$ freshly seeded CEF cells. At various times after infection (0, 12, 24, 48, 72, 96, 120 hr), infected cells were trypsinized and titrated on fresh CEF cells. Numbers of plaques were determined and results represent means of two independent experiments.

A QM7 cell line constitutively expressing MDV-1 gB was obtained by transfection of $1\times10^6$ QM7 cells with 10 μg of pcMgB (FIG. 1), which is based on pcDNA3 (Invitrogen) and contains the MDV-1 gB gene from strain Rispens CV1988 under the control of the human cytomegalovirus immediate early promoter. pcMgB-containing QM7 cells were selected in the presence of 1 mg/ml G418, and gB-expressing clones were identified using anti-gB monoclonal antibody (mab) 2K11 (kindly provided by Dr. Jean-Francois Vautherot, INRA, Tours, France). The resulting cell line expressing MDV-1 gB was termed MgB1.

Construction of MDV-1 BACs. MDV-1 DNA was purified from infected cells by sodium dodecyl sulfate-Proteinase K extraction as described earlier (Morgan et al., 1990). Plasmid pDS-pHA1 was constructed as follows. 2.1 and 3.1 kbp fragments on either side of the MDV-1 Us2 gene (FIG. 1) were amplified by polymerase chain reaction (PCR) using standard primers containing appropriate restriction enzyme sites (Table 1), and both fragments were cloned into pTZ18R (Pharmacia-Amersham). The BAC vector containing the Eco-gpt gene under the control of the HCMV immediate early promoter was released from plasmid pHA1 (kindly provided by Dr. M. Messerle, LMU Munich, Germany; Messerle et al., 1997) and inserted into the PacI sites introduced into both the 2.1 and 3.1 kbp fragment present in plasmid pDS (FIG. 1).

Primary CEF cells were co-transfected with 2 μg 584Ap80C DNA and 10 μg of pDS-pHA1. At 5 days after transfection, cells were plated on primary CEF cells in the presence of 250 μg/ml mycophenolic acid (MPA), 50 μg/ml xanthine and 100 μg/ml hypoxanthine. The MPA/xanthine/hypoxanthine selection was repeated for a total of four times. After complete cytopathic effect (cpe) had developed after the fourth round of selection, viral DNA was prepared from infected cells and 1 μg of infected-cell DNA was electroporated into DHB10 *Escherichia coli* cells. Colonies were detected from 16 hr after transfection on agar plates containing 30 μg/ml chloramphenicol (Sambrook et al., 1989). Single colonies were picked and BAC DNA was prepared from *Escherichia coli* following a standard alkaline lysis protocol (Sambrook et al., 1989). Large-scale preparation of BAC DNA was performed by silica-based affinity chromatography using commercially available kits (Qiagen, Macherey & Nagel). Three MDV-1 584Ap80C BAC clones (BAC19, BAC20, BAC24) were chosen for further analysis.

Mutagenesis of MDV-1 BACs. For mutagenesis of cloned MDV-1 DNA in *Escherichia coli*, recE-catalyzed reactions promoting homologous recombination between linear DNA fragments, referred to as E/T cloning, was performed (Zhang et al., 1998; Narayanan et al., 1999). Plasmid pGETrec (kindly provided by Dr. Panos Ioannou, Murdoch Institute, Melbourne, Australia) harboring the recE, recT and bacteriophage 1 gam gene was transformed into BAC20-containing DH10B cells (Narayanan et al., 1999). After induction of recE, recT and gam by addition of 0.2% arabinose, electrocompetent cells were prepared essentially as described (Narayanan). To delete the gB gene in BAC20, the kanamycin resistance gene ($kan^R$) of plasmid pEGFP-N1 (Clontech) was amplified by PCR. The designed primers contained 50 nucleotide homology arms bordering the desired deletion within gB and 20 nucleotides for amplification of $kan^R$ (Table 1). The resulting 1.6 kbp fragment was purified from an agarose gel (Qiagen) and electroporated in pGETrec-containing BAC20 cells. Colonies harboring the $cam^R$ and $kan^R$ genes were identified on plates containing both antibiotics (Narayanan et al., 1999).

DNA analyses. BAC or viral 584Ap80C DNA was cleaved with EcoRI, BamHI, BglII or StuI and separated on 0.8% agarose gels. DNA fragments were transferred to positively charged Nylon membranes (Pharmacia-Amersham) and Southern blot hybridization was performed using Digoxigenin-labeled BAC19 DNA or individual BamHI fragments of MDV-1 strain GA (Katsuragi-Iwanaga, 1990; Osterrieder, 1999).

In addition, a gB-specific probe from plasmid pcgB and a probe harboring the $kan^R$ gene were prepared for analysis of gB-negative MDV-1 BAC. Chemoluminescent detection of DNA hybrids using CSPD™ was done according to the manufacturer's instruction (Roche Biochemicals).

Indirect immunofluorescence. For indirect immunofluorescence analyses (IIF), cells were grown on 6- or 24-well plates (Greiner Bio-One) or on glass cover slips and subsequently infected where indicated. Cells were fixed with 90% acetone at various times after infection or transfection, and IIF was done exactly as described (Meindl and Osterrieder, 1999). Samples were analyzed by fluorescence microscopy or confocal laser scanning microscopy (CLSM). The antibodies used were anti-gB mab 2K11, anti-pp38 mab H19 (kindly provided by Dr. Lucy Lee, ADOL, East Lansing, Mich.) or a convalescent serum from a chicken infected with MDV-1 (MDSI).

Results:

Construction and analysis of BACs containing complete MDV-1 genomes. One million primary CEF were infected with $1 \times 10^4$ p.f.u. of MDV-1 strain, i.e., infected cells were mixed with uninfected cells. After complete cytopathic effect had developed, DNA was prepared from infected cells and 2 µg viral DNA were transfected into $1 \times 10^6$ primary CEF cells together with 10 µg of pDS-pHA1 plasmid DNA. Five days after transfection, cells were co-seeded with fresh CEF and overlaid with selection medium.

This procedure was repeated for a total of four times. Finally, DNA from recombinant MDV-1 that was able to grow in the presence of MPA/xanthine/hypoxanthine was isolated and subjected to Southern blot analysis using labeled pHA1 as a probe. It could be demonstrated that a portion of the viral DNA contained inserted F plasmid sequences (data not shown). One microgram of this viral DNA was used to transform *Escherichia coil* DH10B cells. Transformed bacteria were plated on agar containing 30 µg/ml chloramphenicol and single colonies were picked. DNA of bacterial colonies was extracted by standard plasmid preparation procedures (Sambrook et al., 1989) and run on 0.8% agarose gels.

Figure 2:
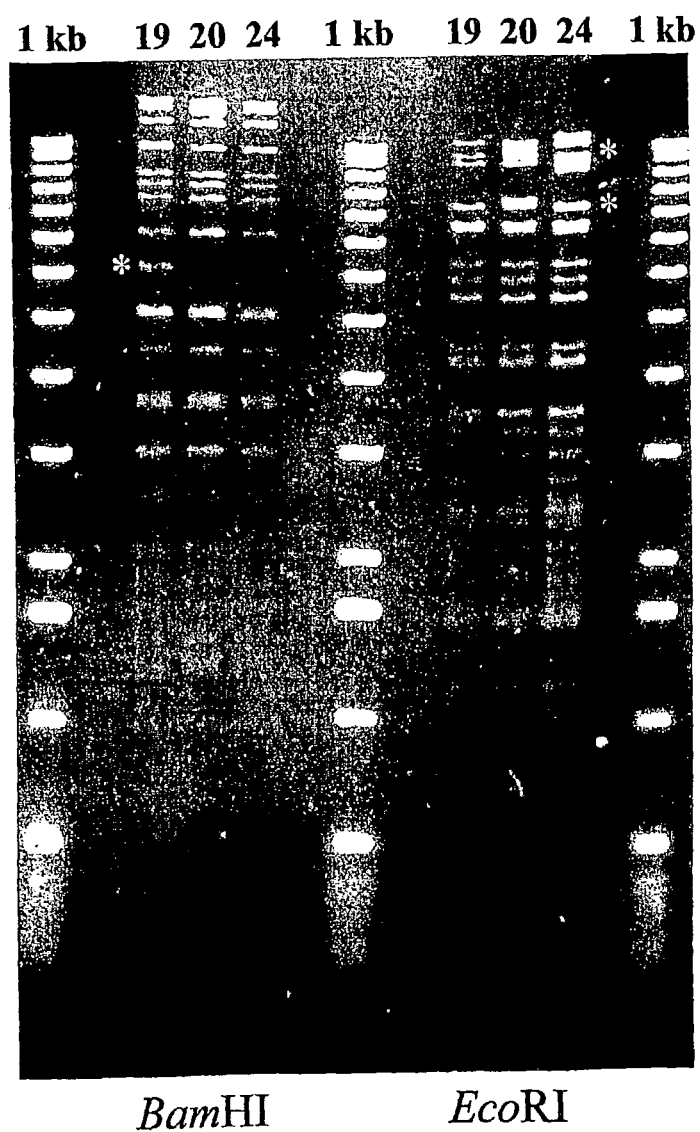
Figure 3:
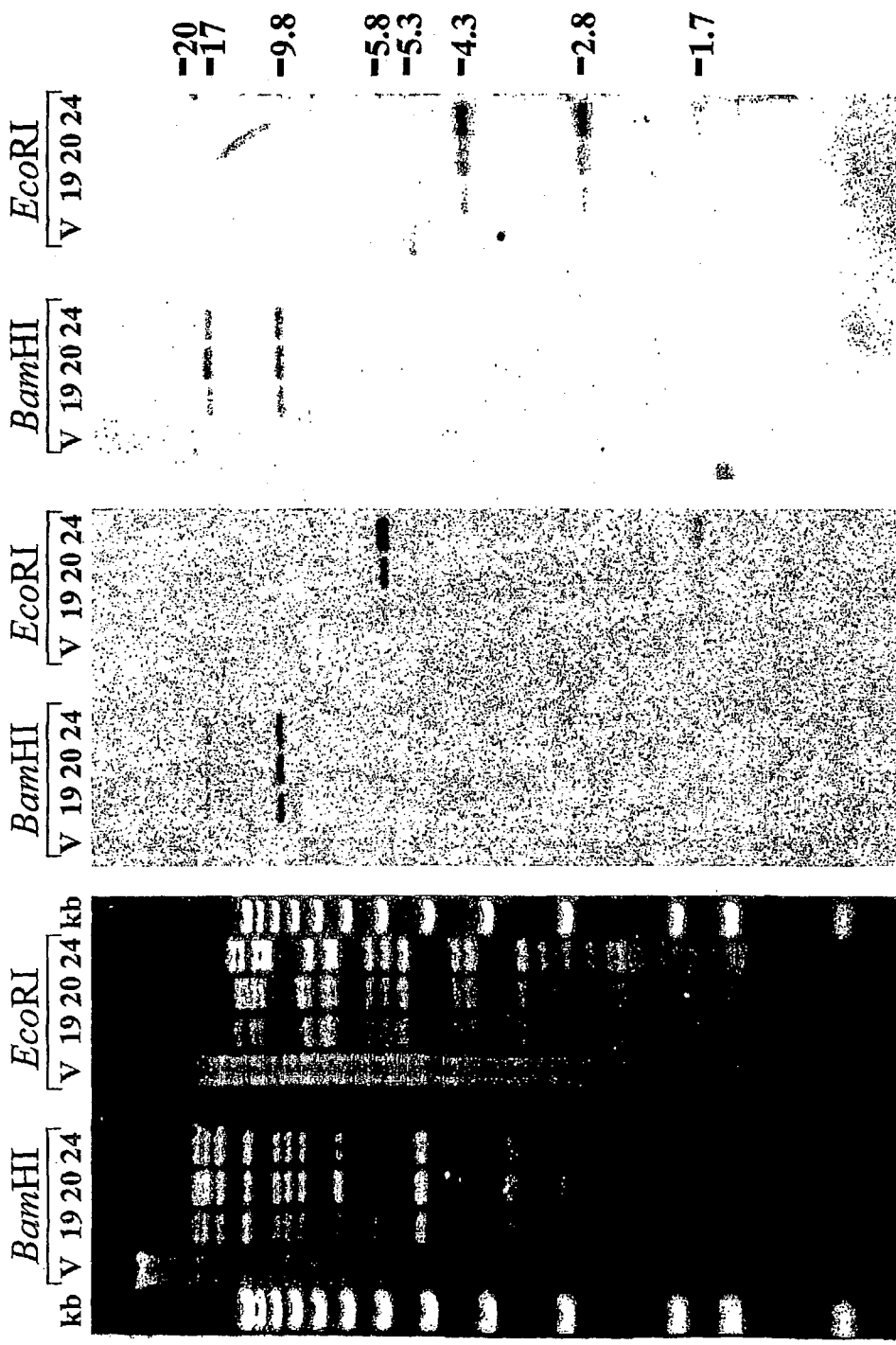

Several of the bacterial colonies were shown to contain high molecular weight extrachromosomal DNA, and three of the clones (BAC19, BAC20 and BAC24) were chosen for further analysis (FIG. 2). To further characterize the isolated BAC clones, Southern blot analysis of 584Ap80C and BAC DNA after cleavage with BamHI or EcoRI with labeled BAC19 DNA as a probe was performed. It could be demonstrated that BAC19, BAC20, and BAC24 DNA exhibited almost identical restriction enzyme fragment patterns when compared to that of the parental 584Ap80C (FIG. 3). Two notable exceptions, however, were readily recognized. The 20 kbp BamHI-A fragment present in 584Ap80C DNA was absent in all analyzed BAC clones. Instead, fragments of 16 and 10 kbp in size were detected in DNA of BAC19, BAC20 and BAC24 (FIG. 3). These two bands represented the enlarged BamHI-A fragment in which, by virtue of insertion of the F plasmid and deletion of Us2 sequences, an additional BamHI site was introduced (FIG. 1).

In EcoRI-digested BAC DNA, one additional band of 5.8 kbp (BAC sequences) and minor alterations in sizes of fragments caused by the deletion of the Us2 gene were observed (FIGS. 1 and 3). The correct insertion of the BAC sequences in the various clones was further analyzed by Southern blot hybridizations using labeled inserts of plasmid pDS or pHA1 as a probe, and the expected reaction pattern in BamHI- or EcoRI-digested DNA was observed. In BamHI-digested BAC DNAs, 16 and 10 kbp BamHI fragments specifically reacted with the pDS probe whereas only the 10 kbp fragment was reactive with a probe derived from plasmid pHA1 (FIG. 1; FIG. 3).

In EcoRI-digested BAC19, BAC20 or BAC24 DNA, fragments of 4.3, 2.8 and 1.7 kbp specifically reacted with the pDS probe, whereas 5.8 and 1.7 kbp fragments specifically hybridized with the pHA1 probe (FIG. 1, FIG. 3). These fragments exactly corresponded to those predicted after insertion of the pHA1 sequences (FIG. 1), and it was concluded that the F plasmid sequences were correctly inserted instead of the Us2 ORF in all MDV-1 BACs analyzed. In addition, some variation in banding patterns of BAC19, BAC20, and BAC24 was noted in either BamHI- or EcoRI-digested DNA, e.g., an additional band of approximately 6.2 kbp in BamHI-digested BAC19 DNA or additional bands in EcoRI-digested DNA of BAC20 and BAC24 (FIGS. 2, 3). To address the question of the observed size variations of individual restriction enzyme fragments, hybridization with the labeled BamHI-D fragment was performed because size variations in the terminal and internal repeats of the unique long region (TRL and IRL) are common.

Figure 4:
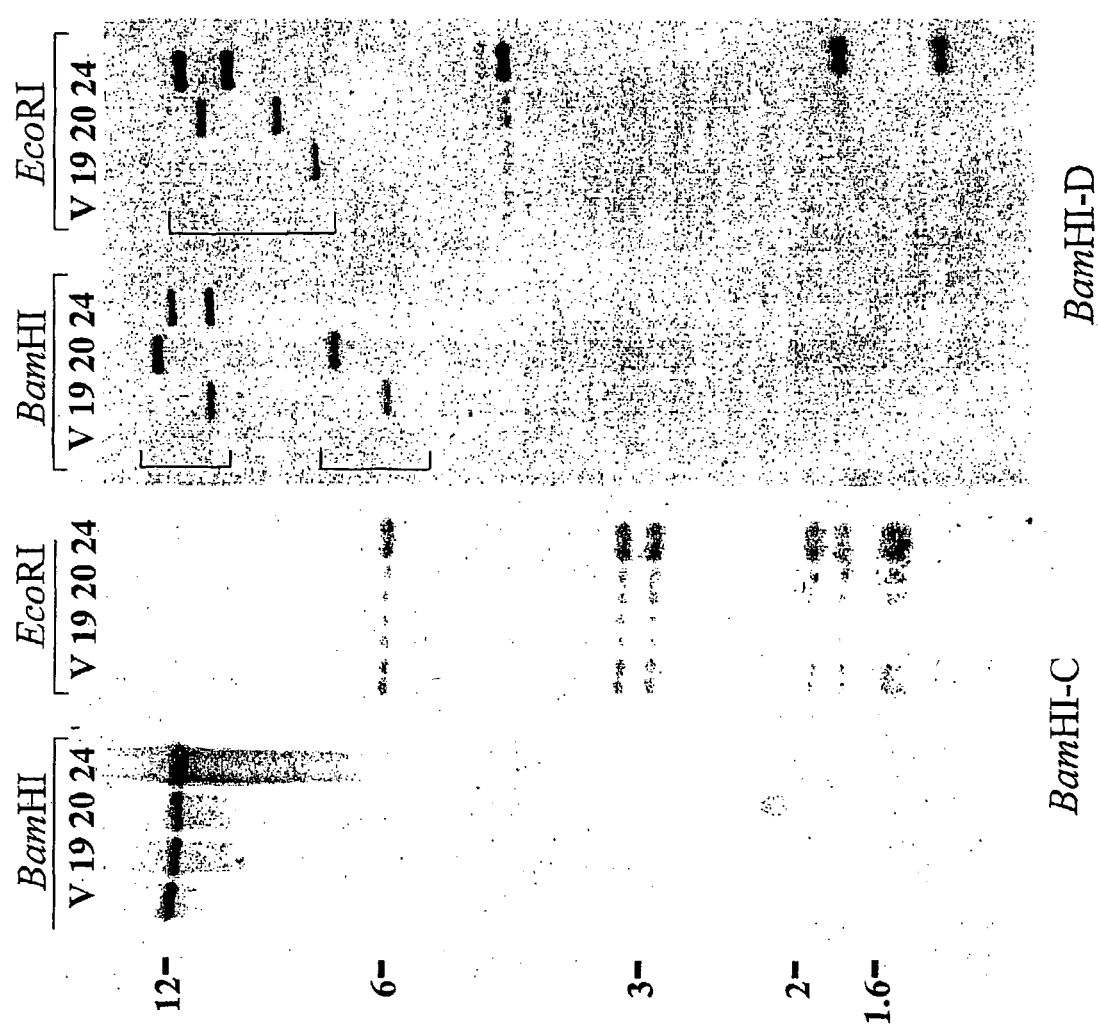
Figure 5:
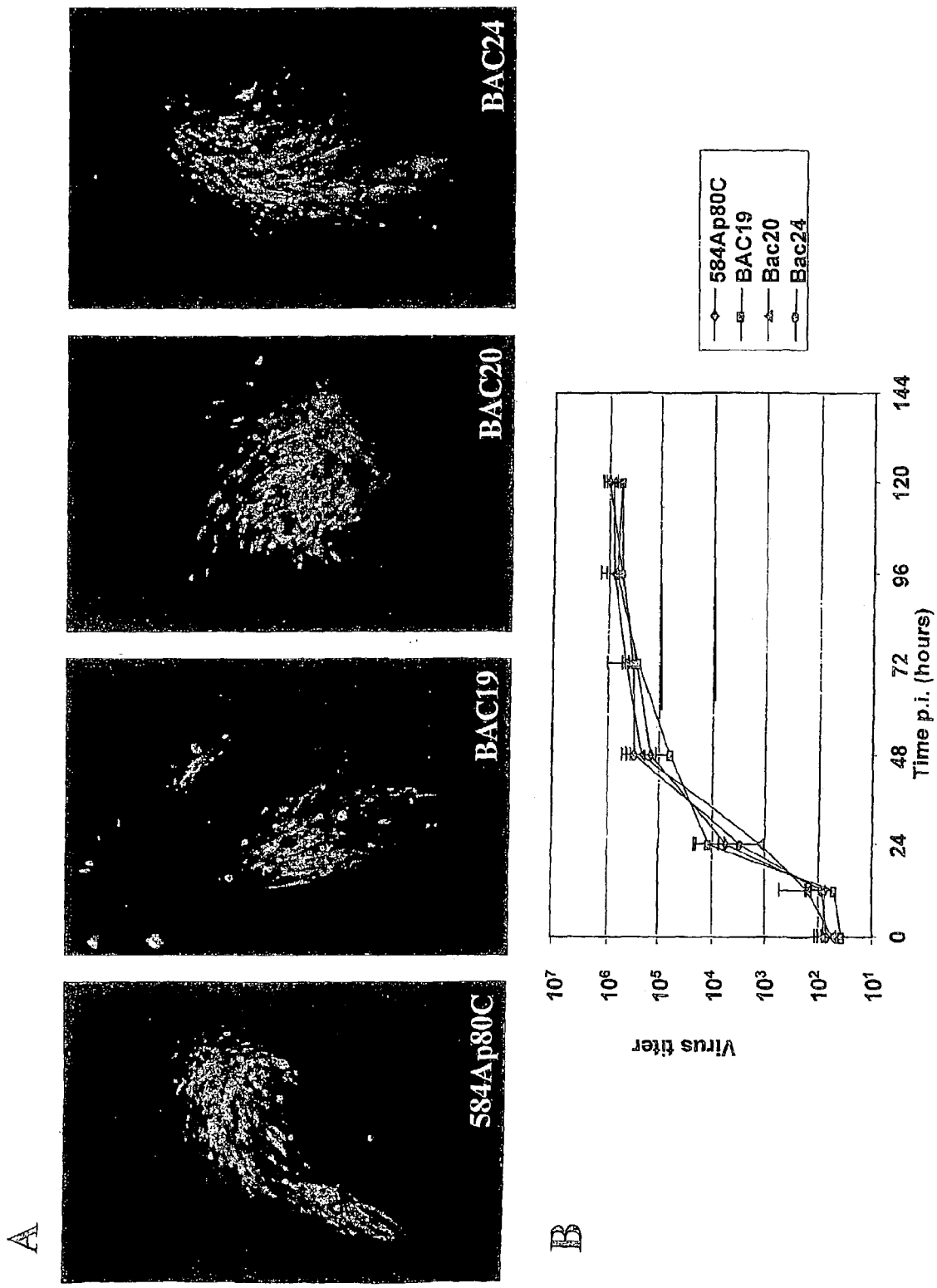
Figure 6:
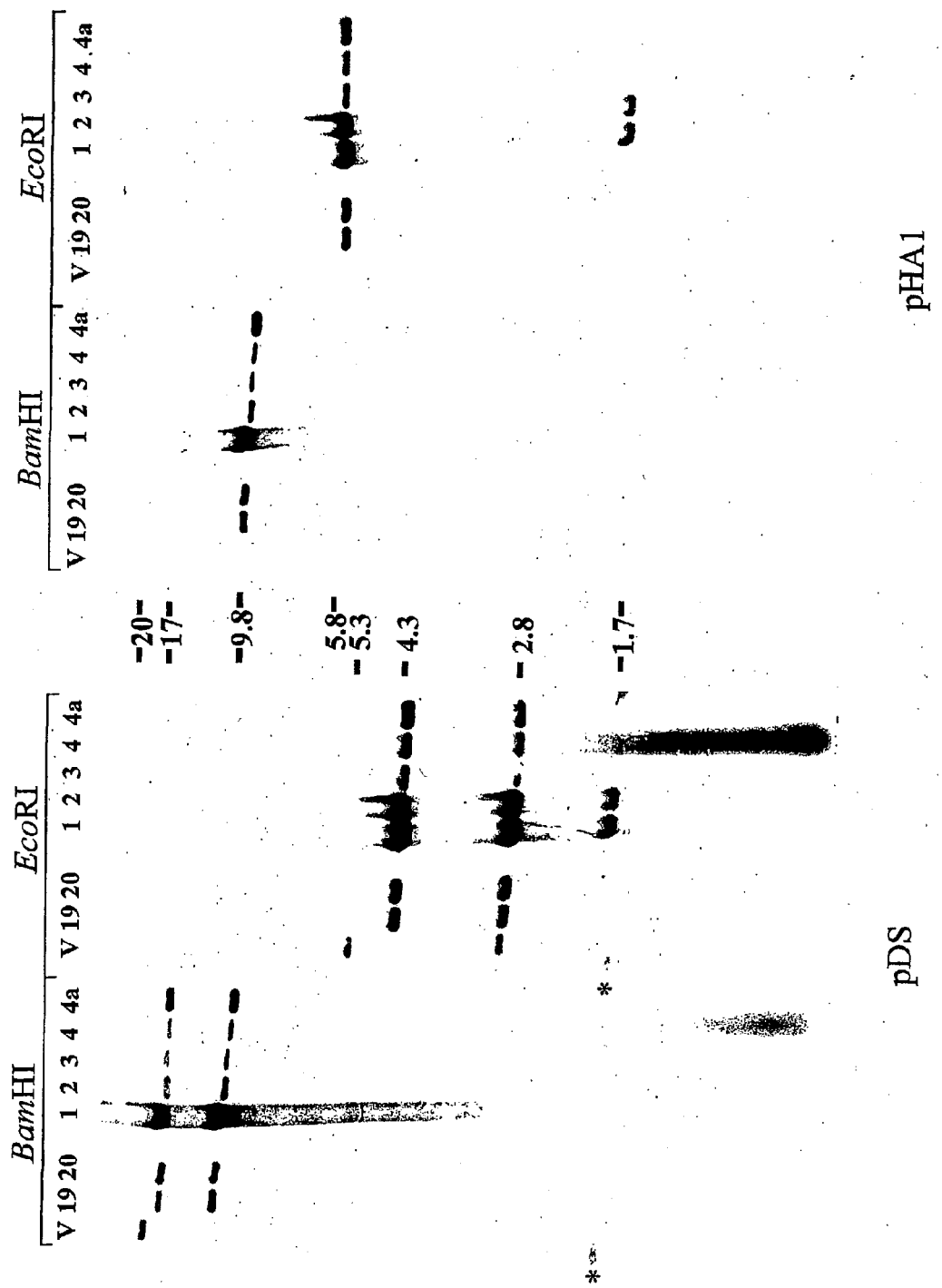
Figure 7:
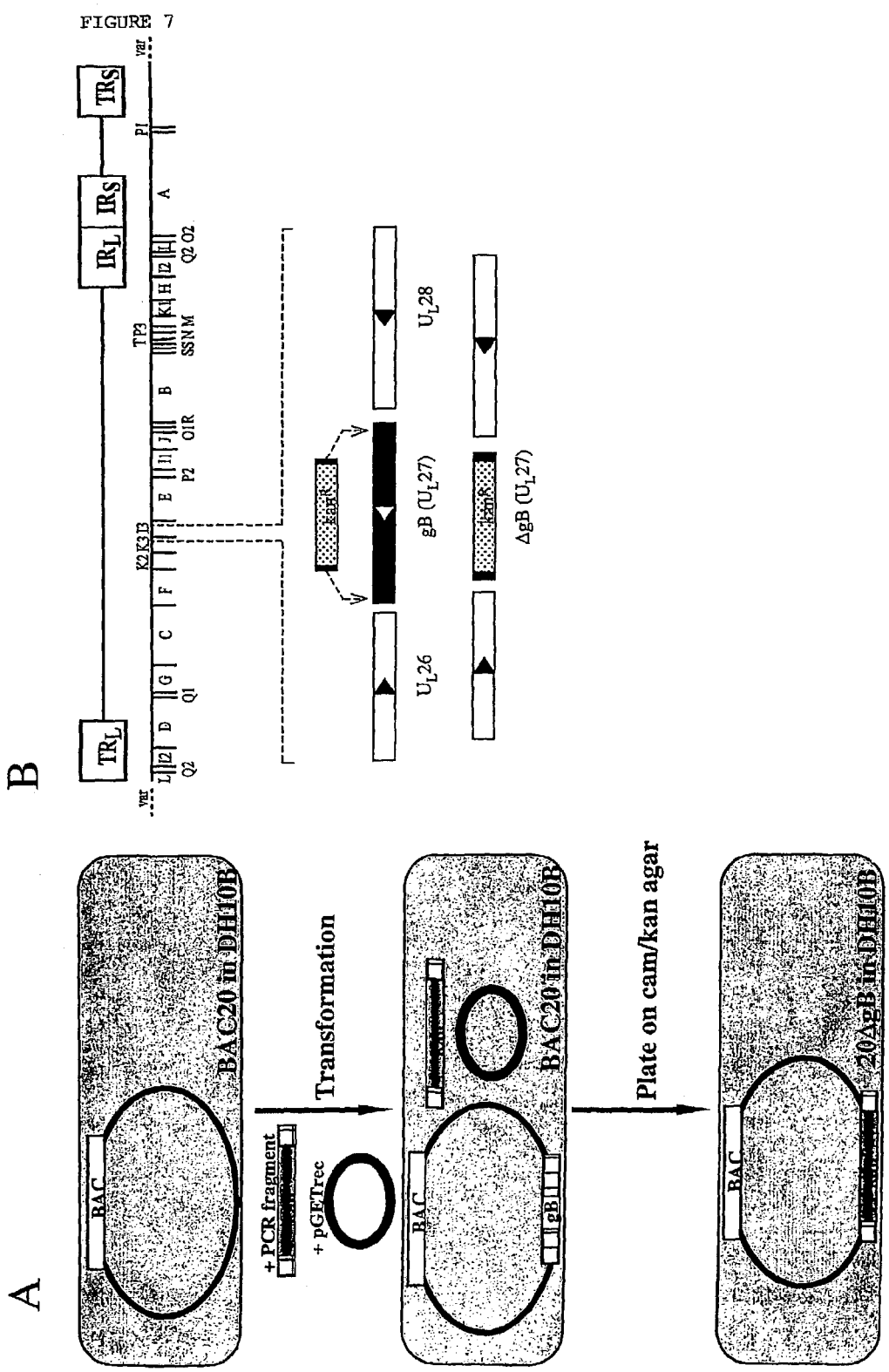
Figure 8:
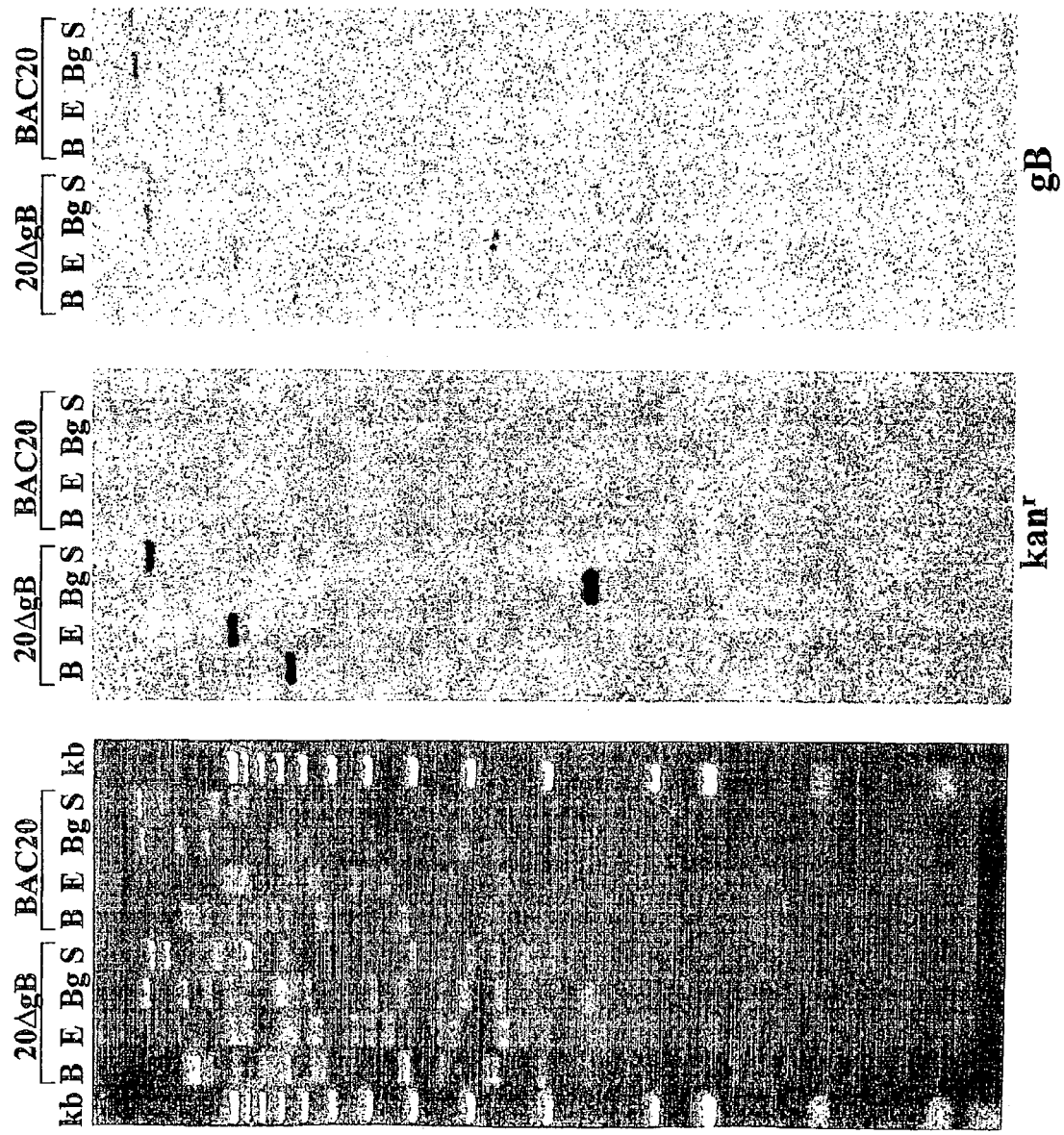
Figure 9:
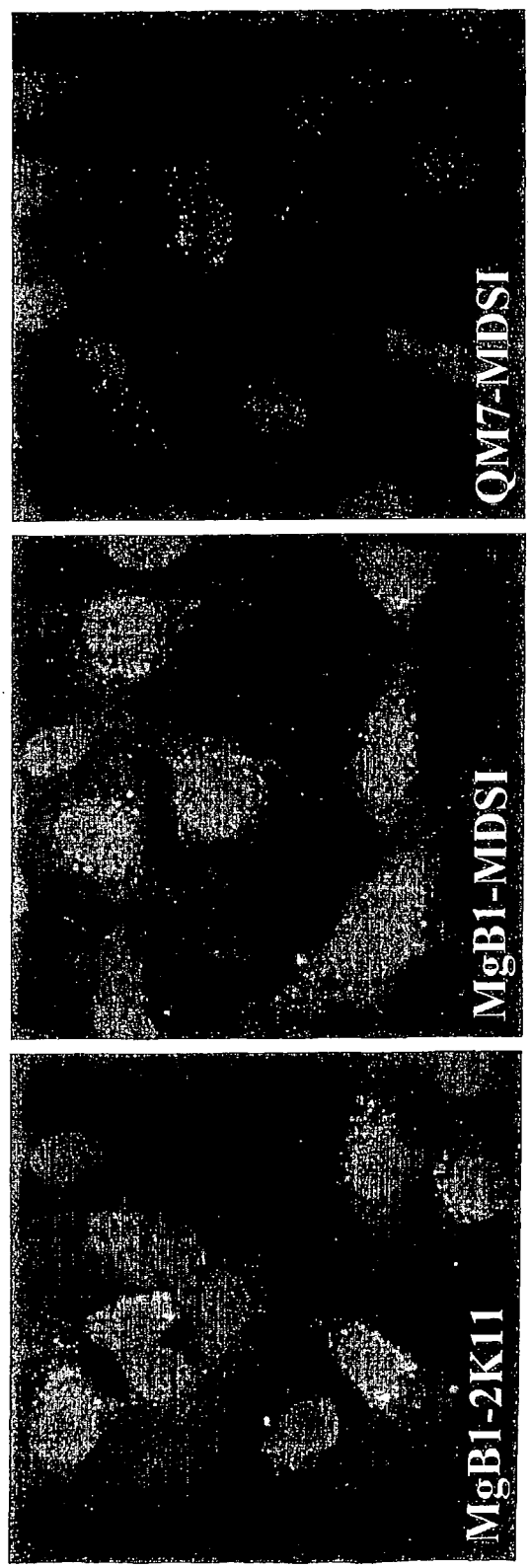
Figure 10:
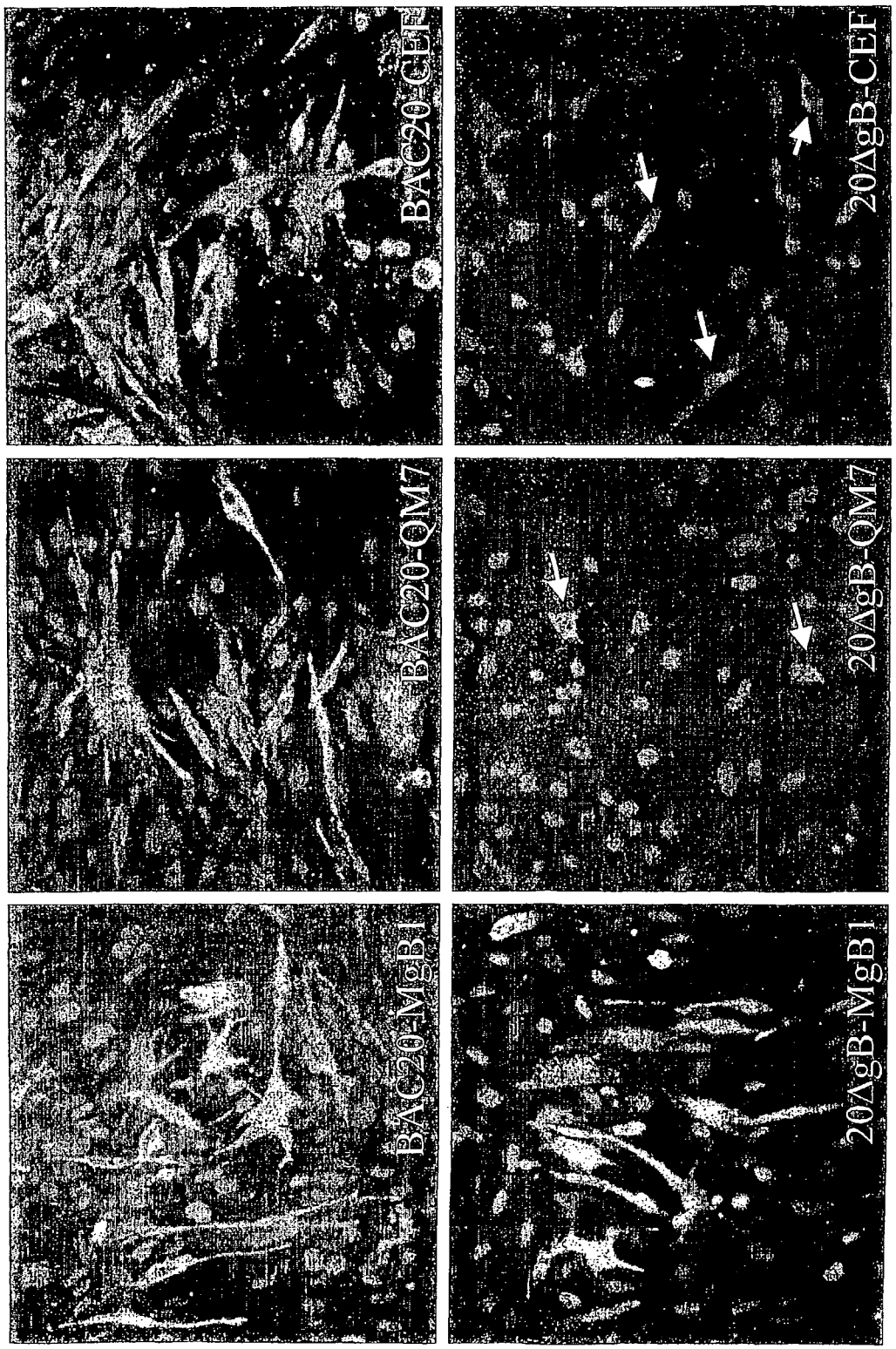

It was shown by Southern blotting that the additional fragments observed in either BamHI- or EcoRI-digested DNA of BAC19, BAC20, or BAC24 resulted indeed from variations in TRL and IRL. Whereas two broad smears with the BamHI-D probe were detected in viral 584Ap80C DNA digested with BamHI which ranged from approximately 9 to 15 kbp and from 4 to 8 kbp (corresponding to the BamHI-D and -H fragments of virulent MDV-1, respectively; FIG. 1), distinct but different bands were observed in all BAC clones analyzed (FIG. 4). All other restriction enzyme fragments of the different BAC clones appeared to be identical with those of viral 584Ap80C DNA. This was confirmed by using several other labeled BamHI fragments as probes, including BamHI-A, -B, -C and -I$_2$ fragments (data for the BamHI-C probe are exemplarily shown in FIG. 4).

Reconstitution of infectious MDV-1 from cloned DNA. DNA of BAC19, BAC20 or BAC24 was transfected into primary CEF. At 3 to 7 days after transfection, MDV-1 specific virus plaques appeared as demonstrated by IIF using anti-MDV-1 gB mab. MDV-1 rescued after transfection of the various BACs was then co-seeded with fresh CEF and sizes of plaques were compared to those induced by parental 584Ap80C. As exemplarily shown for plaques stained on day 2 p.i., no appreciable differences in plaque sizes between recombinant and parental viruses were detected (FIG. 5A).

To further characterize the biological properties of MDV-1 recovered after BAC transfection, growth kinetics of these viruses were compared to that of parental 584Ap80C. In the case of BACs, virus recovered at day 5 after transfection were used to infect fresh CEF cells seeded on 6-well plates (50 p.f.u. of virus were used to infect one well containing $1\times10^6$ cells). Similarly, 50 p.f.u. of 584Ap80C were used to infect fresh CEF in the same way. At various times p.i., virus was harvested and titrated by co-seeding 10-fold virus dilutions with fresh CEF cells. The results of these experiments are summarized in FIG. 5B.

It could be demonstrated that all MDV-1 BACs tested exhibited growth characteristics that were almost identical to those of parental 584Ap80C (FIG. 5B). Maximal titers were reached at 72 hr p.i. and remained virtually constant until the end of the observation period at 120 hr p.i. From the plaque sizes and growth characteristics we concluded that the biological properties of MDV-1 BACs in vitro were virtually indistinguishable from those of the parental strain.

To ascertain stability of the BAC-derived viruses, progeny of BAC transfections of BAC19 and BAC 20 was passaged four times and viral DNA was prepared. Viral DNA was cleaved with BamHI or EcoRI, separated by 0.8% agarose gel electrophoresis, and transferred to Nylon membranes. Hybridization was performed using the pDS or the pHA1 probe. Similar DNA fragments as described above were observed and the banding pattern did not change with serial passage of transfection progeny as analyzed with the two probes (FIG. 6). From these results we concluded that F plasmid-derived sequences remained stably inserted within the 584Ap80C genomes recovered from individual MDV-1 BAC clones even after serial passage in CEF cells.

However, as shown by hybridization with the BamHI-D fragment and PCR analysis, variability of the 132-bp repeat sequences was restored and a diffuse smear of reactive bands was observed in BamHI- or EcoRI-cleaved DNA of transfection progeny already after the first virus passage (data not shown).

Mutagenesis of BAC20 and deletion of gB-encoding sequences. In the next experiments, a recently developed method for mutagenesis of BACs was applied to remove 2.3 kbp of the 2.8 kbp gB gene from BAC20 (FIG. 7). After transformation of plasmid pGETrec (Narayanan) into BAC20-containing DH10B, the $kan^R$ gene was amplified with primers that allowed homologous recombination with MDV-1 gB sequences (Table 1; FIG. 8) and electroporated into BAC20-pGETrec cells. Bacteria were plated on LB agar containing chloramphenicol and kanamycin, and double resistant colonies were picked. After DNA isolation of individual colonies, Southern blot analysis of recombinant BAC20 harboring a deletion within the gB gene (20DgB) was performed. A $kan^{R-}$ and a gB-specific probe detected fragments of 20DgB after cleavage with BamHI, EcoRI, BglII or StuI that were in perfect agreement with those calculated after insertion of the $kan^R$ resistance gene into gB-encoding sequences (FIG. 9). It was noted that—as reported previously—pGETrec, which confers ampicillin resistance, was easily lost from *Escherichia coli* cells grown in the absence of the antibiotic (FIG. 9). From these results we concluded that the gB open reading frame was almost completely removed from 20DgB.

Analysis of gB-negative MDV-1 reconstituted from 20DgB. Because gB is essential for growth of all herpes viruses analyzed to date (reviewed in Pereira), a QM7 cell line which expressed MDV-1 gB under the control of the HCMV immediate early promoter was generated. Indirect immunofluorescence analyses demonstrated that virtually every cell of cell line MgB1 constitutively expressed MDV-1 gB as demonstrated using mab 2K11 or a convalescent chicken serum (MDSI) (FIG. 10). To analyze growth of BAC20 and 20DgB in various cell lines, DNA was prepared and used to transfect CEF, QM7 or MgB1 cells. At 3 to 5 days after transfection, virus plaques were observed in all cells transfected with BAC20 (FIG. 10).

However, after transfection of 20DgB DNA, plaques were observed in gB-expressing MgB1 cells only (FIG. 10). In CEF and QM7 cells transfected with 20DgB, single cells expressed the early pp38 gene as demonstrated by reactivity with mab H19 (Lee et al., but plaque formation was inhibited (FIG. 10). These results of gB being essential for MDV-1 cell-to-cell spread in vitro were confirmed by co-seeding 20DgB-infected MgB1 cells with CEF, QM7 or fresh MgB1 cells. As shown after primary transfection, plaque formation was only observed after co-seeding with gB-expressing cells. From these results we concluded that MDV-1 gB is essentially required for cell-to-cell spread of MDV-1 in cultured cells.

Although Marek's disease virus is an important pathogen of chickens that causes T cell tumors and high mortality in infected animals, little is known about the function of individual genes and gene products in the lytic, latent or tumor phase of the infection. Analysis of MDV-1 genes and gene products has been greatly impaired for two main reasons. Firstly, cultured cells infected with MDV-1 do not yield free infectious virus, and secondly, efficient growth of MDV-1 in cultured cells is restricted to primary or secondary chicken embryo fibroblasts.

Hence, mutagenesis using conventional homologous recombination used to mutagenize other Alphaherpesvirinae is laborious, time-consuming and requires constant supply of primary cells. While mutagenesis of HSV and PrV is certainly facilitated by using the BAC technology, conventional mutagenesis relying on homologous recombination in eukaryotic cells represents a standard technique for these two viruses and numerous mutant viruses have been generated. In contrast, for mutagenesis of MDV-1, BAC cloning and mutagenesis is a major advantage. Once the MDV-1 genome is cloned as a BAC and can be stably maintained in *Escherichia coli*, generation of mutants and analyses of essential genes should be relatively easy. In fact, it was possible to clone the complete genome of strain 584Ap80C as an infectious BAC. Strain 584Ap80C is a descendant of the very virulent plus (vv+) MDV-1 strain 584A after 80 serial passages on CEF cells (Witter, 1997). Analysis of the cloned MDV-1 genomes present in BAC19, BAC20 and BAC24 demonstrated that variations of restriction enzyme patterns were obvious.

This heterogeneity could be attributed to variations in the BamHI-D and -H fragments. It is known that varying numbers of 132-bp tandem repeats are present in various MDV-1 strains and that the number of repeats increases after serial passage in cultured cells (Maotani, Silva, Fukuchi). In addition, the number of the tandem 132-bp repeats was associated with a loss of oncogenicity because a constant number of these units was demonstrated in virulent strains (Fukuchi et al., 1985; Bradley et al., 1989), although recent work on the widely used Rispens CVI 988 vaccine strain demonstrated that there might be no direct correlation of small numbers of the 132-bp repeats and virulence. In the case of MDV-1 strain 584Ap80C, hybridization of restriction enzyme-digested viral DNA with the BamHI-D fragment yielded diffuse banding patterns indicating a variable number of repeats present in the virus population. In contrast, only single strongly reactive bands were identified in each of the BAC clones with the same probe. However, the sizes of reactive bands after cleavage with BamHI or EcoRI varied between BAC19, BAC20 and BAC24, indicating that genomes containing different numbers of the 132-bp repeats had been cloned. This interpretation was substantiated by PCR analyses targeting the 132-bp repeats. Whereas the typical ladder-like appearance of PCR products was obtained with DNA of 584Ap80C (Becker et al., 1993), distinct bands were amplified from cloned viral DNA in the case of BAC19, BAC20 or BAC24.

It was therefore concluded that the variable restriction enzyme patterns of the different BAC clones resulted from various numbers of tandem 132-bp repeats present in the individual clones which did not influence the infectivity of the cloned DNA because infectious virus was recovered after transfection of DNA isolated from each of the different BAC clones.

After cloning of the complete MDV-1 genome and proof of infectivity of cloned MDV-1 DNA, a recently developed mutagenesis system in which a linear DNA fragment can be recombined into bacteria-resident DNA and which is catalyzed by recE (Narayanan, Muyrers) was used to delete gB-encoding sequences of BAC20. The mutagenesis is based on recE, recT and the recB/C-suppressing λ gam gene present on plasmid pGETrec (Narayanan et al., 1999).

The big advantages of the system that was used for the first time to manipulate a virus genome are: (i) only 30 to 50 bp homology arms are needed to target a specific sequence to be deleted, i.e., deletion of any open reading frame can be achieved without the need to clone recombination cassettes, (ii) the method is very fast, and (iii) the pGETrec vector conferring the mutagenesis system and expressing ampicillin resistance is rapidly lost from bacterial cells in the absence of ampicillin. After electroporation of the gB knockout PCR product into pGETrec-containing BAC20 cells, between 10 and 30 $cam^R$ and $kan^R$ double-resistant colonies were obtained. One of the colonies was termed 20DgB-1 and chosen for further analyses because it had lost pGETrec immediately after plating on agar containing chloramphenicol and kanamycin.

Southern blot analyses demonstrated successful deletion of the gB gene and the insertion of the $kan^R$ gene in 20DgB-1. MDV-1 recovered after transfection of CEF cells with 20DgB-1 was unable to spread from infected cells to neighboring cells, indicating that MDV-1 gB, like its counterparts in other herpes viruses, is essential for cell-to-cell spread of infectivity. Because MDV-1 is highly cell-associated in cultured cells and does not release infectious virus to the culture medium, we were not able to investigate a possible role of MDV-1 gB in virus entry. The generated gB mutant represents the first example of an MDV-1 with deletion of an essential gene and demonstrates the power of the BAC cloning and mutagenesis system which is especially useful in the case of MDV-1. Using MDV-1 BAC and the permanent cell line QM7 which allows MDV-1 propagation and which—unlike quail fibroblast QT35 cell line—does not harbor MDV-1 sequences (Majerciak, 2001), represents an excellent combination to thoroughly analyze essential MDV-1 genes. In addition, comparative analyses on gene functions of various Alphaherpesvirinae can now include MDV-1 and allows studies on very distantly related members, such as VZV or BHV-4 of one viral family.

With the cloned genomes as provided herein in at hand, a detailed further assessment of lytic, latent and tumor-inducing genes is provided for virus in which genetic manipulations used to be very restricted.

REFERENCES

1. Anderson, A. S., Parcells, M. S., and R. W. Morgan. 1998. The glycoprotein D (US6) homolog is not essential for oncogenicity or horizontal transmission of Marek's disease virus. *J Virol.* 72: 2548-2553.
2. Becker, Y., E. Tabor, Y. Asher, I. Davidson, M. Malkinson, and R. L. Witter. 1993. PCR detection of amplified 132 bp repeats in Marek's disease virus type 1 (MDV-1) DNA can serve as an indicator for critical genomic rearrangement leading to the attenuation of virus virulence. *Virus Genes* 7: 277-287.
3. Borst, E. M., G. Hahn, U. H. Koszinowski, and M. Messerle. 1999. Cloning of the human cytomegalovirus (HCMV) genome as an infectious bacterial artificial chromosome in *Escherichia coli*: a new approach for construction of HCMV mutants. *J. Virol.* 73: 8320-8329.
4. Bradley, G., M. Hayashi, G. Lancz, A. Tanaka, and M. Nonoyama. 1989. Structure of the Marek's Disease virus BamHI-H gene family: Genes of putative importance for tumor induction. *J. Virol.* 63: 2534-2542.
5. Bradley, G., G. Lancz, A. Tanaka, and M. Nonoyama. 1989. Loss of Marek's disease virus tumorigenicity is associated with truncation of RNAs transcribed within BamHI-H. *J. Virol.* 63: 4129-4235.
6. Brune, W., C. Menard, U. Hobom, S. Odenbreit, M. Messerle, and U. H. Koszinowski. 1999. Rapid identification of essential and nonessential herpes virus genes by direct transposon mutagenesis. *Nat. Biotechnol.* 17:360-364.
7. Brunovskis, P., and L. F. Velicer. 1995. The Marek's disease virus (MDV) unique short region: alphaherpes virus-homologous, fowlpox virus-homologous, and MDV-specific genes. *Virology* 206: 324-38.
8. Cantello, J. L., A. S. Anderson, A. Francesconi, and R. W. Morgan. 1991. Isolation of a Marek's disease virus (MDV) recombinant containing the lacZ gene of *Escherichia coli* stably inserted within the MDV US2 gene. *J. Virol.* 65:1584-1588.
9. Cui, Z. Z., D. Yan, and L. F. Lee. 1990. Marek's disease virus gene clones encoding virus-specific phosphorylated polypeptides and serological characterization of fusion proteins. *Virus Genes* 3:309-322.
10. Delecluse, H. J., T. Hilsendegen, D. Pich, R. Zeidler, and W. Hammerschmidt. 1998. Propagation and recovery of intact, infectious Epstein-Barr virus from prokaryotic to human cells. *Proc. Natl. Acad. Sci. U.S.A.* 95: 8245-8250.
11. Fukuchi, K., M. Sudo, Y. S. Lee, A. Tanaka, and M. Nonoyama. 1984. Structure of Marek's disease virus DNA: detailed restriction enzyme map. *J. Virol.* 51: 102-109.
12. Lee, L. F., P. Wu, D. Sui, D. Ren. J. Kamil, H. J. Kung, and R. L. Witter. 2000. The complete unique long sequence and the overall genomic organization of the GA strain of Marek's disease virus. *Proc. Natl. Acad. Sci. U.S.A.* 97:6091-6096.

13. Maotani, K., K. Kanamori, K. Ikuta, S. Ueda, S. Kato, and K. Hirai. 1986. Amplification of a tandem repeat within inverted repeats of Marek's disease virus DNA during serial in vitro passage. *J. Virol.* 58: 657-659.
14. Meindl, A. and N. Osterrieder. 1999. The equine herpes virus type 1 Us2 homolog encodes a nonessential membrane-associated virion component. *J. Virol.* 73, 3430-3437.
15. Messerle, M., I. Crnkovic, W. Hammerschmidt, H. Ziegler, and U. H. Koszinowski. 1997. Cloning and mutagenesis of a herpes virus genome as an infectious bacterial artificial chromosome. *Proc. Natl. Acad. Sci. U.S.A.* 94: 14759-14763.
16. Morgan, R. W., J. L. Cantello, and C. H. McDermott. 1990. Transfection of chicken embryo fibroblasts with Marek's disease virus DNA. *Avian Dis.* 34:345-351.
17. Muyrers, J. P., Y. Zhang, G. Testa, and A. F. Stewart. 1999. Rapid modification of bacterial artificial chromosomes by ET-recombination. *Nucleic Acids Res.* 27: 1555-1557.
18. Narayanan, K., R. Williamson, Y. Zhang, A. F. Stewart, and P. A. Ioannou. 1999. Efficient and precise engineering of a 200 kb beta-globin human/bacterial artificial chromosome in *E. coli* DH10B using an inducible homologous recombination system. *Gene Ther.* 6: 442-447.
19. Osterrieder, N. 1999. Sequence and initial characterization of the $U_L10$ (glycoprotein M) and $U_L11$ homologous genes of serotype 1 Marek's Disease Virus. *Arch. Virol.* 144, 1853-63.
20. Osterrieder, N., A. Neubauer, C. Brandmüller, B. Braun, O.-R. Kaaden, and J. D. Baines. 1996. The equine herpes virus type 1 glycoprotein gp21/22a, the herpes simplex virus type 1 gM-homolog, is involved in virus penetration and cell-to-cell spread of virions. *J. Virol* 70: 4110-4115.
21. Parcells, M. S., A. S. Anderson, J. L. Cantello, and R. W. Morgan. 1994. Characterization of Marek's disease virus insertion and deletion mutants that lack US1 (ICP22 homolog), US10, and/or US2 and neighboring short-component open reading frames. *J. Virol.* 68: 8239-8253.
22. Parcells, M. S., A. S. Anderson, and R. W. Morgan. 1994. Retention of oncogenicity by a Marek's disease virus mutant lacking six unique short region genes. *J. Virol.* 69: 7888-7898.
23. Parcells, M. S., A. S. Anderson, and R. W. Morgan. 1994. Characterization of a Marek's disease virus mutant containing a lacZ insertion in the US6 (gD) homologue gene. *Virus Genes* 9:5-13.
24. Payne, L. N. 1985. Pathology. In: LN Payne (ed) Marek's Disease. Kluwer Academic Publishers, Hingham, Mass., U.S.A., pp. 43-76.
25. Pereira, L. 1994. Function of glycoprotein B homologues of the family herpesviridae. *Infect. Agents Dis.* 3: 9-28.
26. Ross, N. L. J., Binns, M. M., and J. Pastorek. 1991. DNA sequence and organization of genes in a 5.5 kbp EcoRI fragment mapping in the short unique segment of Marek's disease virus (strain RB1B). *J. Gen. Virol.* 72: 949-954.
27. Sakaguchi, M., T. Urakawa, Y. Hirayama, N. Miki, M. Yamamoto, G. S. Zhu, and K. Hirai. 1993. Marek's disease virus protein kinase gene identified within the short unique region of the viral genome is not essential for viral replication in cell culture and vaccine-induced immunity in chickens. *Virology* 195: 140-148.
28. Sambrook, J., D. F. Fritsch, and T. Maniatis. 1989. Molecular Cloning: A Laboratory Manual. Cold Spring Harbor Laboratory Press, Cold Spring Harbor.
29. Schat, K. A. 1985. Characteristics of the virus. In: L N Payne (ed) Marek's Disease. Kluwer Academic Publishers, Hingham, Mass., U.S.A., pp. 77-112.
30. Schat, K. A., B. J. van Iddekinge, H. Boerrigter, P. H. O'Connell, and G. Koch. 1998. Open reading frame L1 of Marek's disease herpes virus is not essential for in vitro and in vivo virus replication and establishment of latency. *J. Gen. Virol.* 79: 841-849.
31. Silva, R. F., and R. L. Witter. 1985. Genomic expansion of Marek's disease virus DNA is associated with serial in vitro passage. *J. Virol.* 54: 690-696.
32. Smith G. A., and L. W. Enquist. 1999. Construction and transposon mutagenesis in *Escherichia coli* of a full-length infectious clone of pseudorabies virus, an alphaherpes virus. *J. Virol.* 73: 6405-6414.
33. Smith, G. A., and L. W. Enquist. 2000. A self-recombining bacterial artificial chromosome and its application for analysis of herpes virus pathogenesis. *Proc. Natl. Acad. Sci. U.S.A.* 97: 4873-4878.
34. Suter, M., A. M. Lew, P. Grob, G. J. Adema, M. Ackermann, K. Shortman, and C. Fraefel. 1999. BAC-VAC, a novel generation of (DNA) vaccines: A bacterial artificial chromosome (BAC) containing a replication-competent, packaging-defective virus genome induces protective immunity against herpes simplex virus 1. *Proc. Natl. Acad. Sci. U.S.A.* 96: 12697-12702.
35. van Iddekinge, B. J., L. Stenzler, K. A. Schat, H. Boerrigter, and G. Koch. 1999. Genome analysis of Marek's disease virus strain CVI-988: effect of cell culture passage on the inverted repeat regions. i Avian Dis. 43:182-188.
36. van Regenmortel, M. H. V., C. M. Fauquet, D. H. L. Bishop, E. Carstens, M. K. Estes, S. Lemon, J. Maniloff, Mass. Mayo, D. McGeoch, C. R. Pringle, and R. B. Wickner (eds). 1999. Virus Taxonomy. Seventh Report of the International Committee on Taxonomy of Viruses. Academic Press, New York, San Diego.
37. Wagner, M., S. Jonjic, U. H. Koszinowski, and M. Messerle. 1999. Systematic excision of vector sequences from the BAC-cloned herpes virus genome during virus reconstitution. *J. Virol.* 73:7056-7060.
38. Witter, R. L. 1985. Principles of vaccination. In: L. N. Payne (ed): Marek's Disease. Kluwer Academic Publishers, Hingham, Mass., U.S.A., pp. 203-250.
39. Witter R. L. 1997. Increased virulence of Marek's disease virus field isolates. *Avian Dis.* 41: 149-163.
40. Witter, R. L., J. M. Sharma, and A. M. Fadly. 1980. Pathogenicity of variant Marek's disease virus isolants in vaccinated and unvaccinated chickens. *Avian Dis.* 24: 210-232.
41. Zhang, Y., F. Buchholz, J. P. Muyrers, and A. F. Stewart. 1998. A new logic for DNA engineering using recombination in *Escherichia coli*. *Nature Genet.* 20:123-128.

TABLE 1

Primers used for generation of plasmids pDS and pcMgB and for deletion of gB

| Primer | Sequence | Fragment/plasmid Generated |
|---|---|---|
| MUS21 | 5'-ACAggattcCGTGTTTGAATACTGG-3'[a] | (SEQ ID NO:1) 2.1 kb pDS |
| MUS22 | 5'-ATAgtcgacTttaattaaCCGGTAGTCATTAGC-3' | (SEQ ID NO:2) 2.1 kb pDS |
| MUS23 | 5'-ATCgcatgcTTAATTAATTTGGCAAAACGGAATAGG-3' | (SEQ ID NO:3) 3.1 kb pDS |

TABLE 1-continued

Primers used for generation of plasmids pDS and pcMgB and for deletion of gB

| Primer | Sequence | Fragment/plasmid Generated |
|---|---|---|
| MUS24 | 5'-CGCaagcttAATATGAATCTCTAAAACTTCTCGGC-3' | (SEQ ID NO:4) 3.1 kb pDS |
| gB-up | 5'-GATAgaatccATGCACTATTTTAGGCGG-3' | (SEQ ID NO:5) pcMgB |
| gB-low | 5'-ATACctcgagTTACACAGCATCATCTTCTG-3' | (SEQ ID NO:6) pcMgB |
| gBkana | 5'-*TTTTCTTTCATCAATAGATGTTCGTTCCAAATCATCTGATT CCTCGCCAT*<u>AAAGCACTAAATCGGAACCCTAAAGGGAGC</u>-3'[b] | (SEQ ID NO:7) kan[R] gene for gB deletion |
| gBkanb | 5'-*ATATAGACAGATCACTAATCGATATACAGATAGGACGCC CGTTTCCATTG*<u>ATTGTCTCCTTCCGTGTTTCAGTTAGCCTC</u>-3' | (SEQ ID NO:8) kan[R] gene for gB deletion |

[a] Bold sequences indicate restriction enzyme sites, sequences in italics indicate additional bases not present in the MDV-1 sequence.
[b] Underlined sequences indicate sequences from pEGFP-N1 used to amplify the kan[r] gene, bold and underlined sequences indicate gB sequences used for homologous recombination and recE/T-mediated deletion of gB.

What is claimed is:

1. A composition comprising:
a genomic nucleic acid molecule comprising a replicative full-length copy of a Marek's Disease Virus-1 (MDV-1) herpesvirus genome, except in that the US2 coding sequence of the MDV-1 herpesvirus genome is replaced by a bacterial artificial chromosome (BAC) vector;
wherein said genomic nucleic acid molecule is capable of replication in a eukaryotic host cell;
wherein said genomic nucleic acid molecule encodes infectious MDV-1 herpesvirus when the genomic nucleic acid molecule is expressed in a host cell; and
wherein said BAC vector allows for recombination of the genomic nucleic acid in a bacterium.

2. The composition of claim 1 wherein said MDV-1 herpesvirus genome has an additional functional deletion in a gene different from US2.

3. The composition of claim 1 wherein said replicative genome is of a MDV-1 herpesvirus that is a virulent, a very virulent, or a very virulent plus field virus.

4. A method of inducing an immune response in a subject, said method comprising:
administering to the subject a composition of claim 1.

5. A method for limiting the risks of a subject acquiring or fully manifesting a disease caused by an infection with a strictly host cell-associated Marek's Disease Virus-1 (MDV-1) herpesvirus, said method comprising administering to the subject the composition of claim 1.

6. The method according to claim 5 wherein said subject is a bird.

7. A nucleic acid comprising:
a nucleotide sequence that is a replicative genome of a Marek's Disease Virus-1 (MDV-1) herpesvirus; and
a bacterial artificial chromosome (BAC) vector sequence;
wherein the replicative genome of a Marek's Disease Virus-1 (MDV-1) herpesvirus comprises a full-length copy of a MDV-1 herpesvirus genome except in that the US2 coding sequence is replaced by the BAC vector;
wherein the nucleic acid is capable of replication in a eukaryotic host cell;
wherein the nucleic acid encodes infectious MDV-1 herpesvirus when the nucleic acid is expressed in a host cell; and
wherein the BAC vector sequence allows for recombination of the nucleic acid in a bacterium.

* * * * *

UNITED STATES PATENT AND TRADEMARK OFFICE
CERTIFICATE OF CORRECTION

| | | |
|---|---|---|
| PATENT NO. | : 9,073,979 B2 | Page 1 of 1 |
| APPLICATION NO. | : 10/354932 | |
| DATED | : July 7, 2015 | |
| INVENTOR(S) | : Frank Fehler and Klaus Osterrieder | |

It is certified that error appears in the above-identified patent and that said Letters Patent is hereby corrected as shown below:

References Cited

Other Publications, page 1, column 2, line 4, Delete "EPO1" and insert -- EP01 --, therefor.

Other Publications, page 1, column 2, line 43, Delete "Dorsal" and insert -- Bursal --, therefor.

Signed and Sealed this
First Day of December, 2015

Michelle K. Lee
*Director of the United States Patent and Trademark Office*